(12) United States Patent
Madden

(10) Patent No.: US 10,864,248 B2
(45) Date of Patent: Dec. 15, 2020

(54) DAB2 INHIBITORS FOR THE PREVENTION AND TREATMENT OF CYSTIC FIBROSIS

(71) Applicant: Trustees of Dartmouth College, Hanover, NH (US)

(72) Inventor: Dean R. Madden, Hanover, NH (US)

(73) Assignee: TRUSTEES OF DARTMOUTH COLLEGE, Hanover, NH (US)

( * ) Notice: Subject to any disclaimer, the term of this patent is extended or adjusted under 35 U.S.C. 154(b) by 742 days.

(21) Appl. No.: 15/526,392

(22) PCT Filed: Nov. 11, 2015

(86) PCT No.: PCT/US2015/060071
§ 371 (c)(1),
(2) Date: May 12, 2017

(87) PCT Pub. No.: WO2016/077413
PCT Pub. Date: May 19, 2016

(65) Prior Publication Data
US 2017/0304392 A1    Oct. 26, 2017

Related U.S. Application Data

(60) Provisional application No. 62/078,499, filed on Nov. 12, 2014.

(51) Int. Cl.
| A61K 38/10 | (2006.01) |
| A61K 31/4196 | (2006.01) |
| A61K 31/56 | (2006.01) |
| C07K 7/08 | (2006.01) |
| C07K 14/47 | (2006.01) |
| C07K 14/705 | (2006.01) |
| A61K 9/00 | (2006.01) |
| A61K 31/4439 | (2006.01) |
| A61K 31/473 | (2006.01) |
| A61K 31/4745 | (2006.01) |
| A61K 31/519 | (2006.01) |
| A61K 31/565 | (2006.01) |
| A61K 45/06 | (2006.01) |
| A61K 38/00 | (2006.01) |

(52) U.S. Cl.
CPC .............. *A61K 38/10* (2013.01); *A61K 9/007* (2013.01); *A61K 31/4196* (2013.01); *A61K 31/4439* (2013.01); *A61K 31/473* (2013.01); *A61K 31/4745* (2013.01); *A61K 31/519* (2013.01); *A61K 31/56* (2013.01); *A61K 31/565* (2013.01); *A61K 45/06* (2013.01); *C07K 7/08* (2013.01); *C07K 14/4712* (2013.01); *C07K 14/705* (2013.01); *A61K 38/00* (2013.01)

(58) Field of Classification Search
CPC .... A61K 31/4196; A61K 31/56; A61K 38/10; C07K 7/08
See application file for complete search history.

(56) References Cited

U.S. PATENT DOCUMENTS

| 4,427,669 A | * | 1/1984 | Blake | A61K 31/565 |
| | | | | 514/182 |
| 2004/0170601 A1 | * | 9/2004 | Strom | A61K 2300/00 |
| | | | | 424/85.1 |
| 2006/0141046 A1 | * | 6/2006 | Cattaneo | A61K 9/1652 |
| | | | | 424/489 |
| 2007/0197488 A1 | * | 8/2007 | Peters | C07J 41/0044 |
| | | | | 514/171 |
| 2011/0271957 A1 | * | 11/2011 | Matis | A61K 31/57 |
| | | | | 128/203.12 |
| 2015/0133421 A1 | * | 5/2015 | Bernick | A61K 31/565 |
| | | | | 514/182 |

FOREIGN PATENT DOCUMENTS

| CA | 1119603 | 3/1982 |
| WO | WO 2008/121877 A2 | 10/2008 |

OTHER PUBLICATIONS

Wong, et al. (Azithromycin for prevention of exacerbations in non-cystic fibrosis bronchiectasis (EMBRACE): a randomised, double-blind, placebo-controlled trial, Lancet 2012; 380: 660-67) (Year: 2012).*
Glushkov et al. Synthesis and Antiinflammatory and Analgesic Activity of Amidines of 3,4-Dihydroisoquinoline Series. Pharmaceutical Chemistry Journal. 2005, vol. 39, No. 10, pp. 533-536. (Year: 2005).*
European Extended Search Report dated Jul. 13, 2018 issued in EP 15859191.7 filed Nov. 11, 2015.
Bachmann et al. "The Synthesis of Analogs of the Sex Hormones. An Analog of Equilenin Lacking the Phenolic A Ring" (1941) Journal of the American Chemical Society 63(2)598-602.
Bertrand, et al. "The role of regulated CFTR trafficking in epithelial secretion" (2003) *Am. J. Physiol. Cell Physiol.* 285(1):C1-18.
Boucher "New concepts of the pathogenesis of cystic fibrosis lung disease" (2004) *Eur. Respir. J.* 23:146-158.
Cai, et al. "Synthesis of Novel Tricyclic Aryltriazole-3-Thione Compounds" (2005) *Synthetic Communications* 35: 349-356.
Cheng, et al. "Defective intracellular transport and processing of CFTR is the molecular basis of most cystic fibrosis" (1990) *Cell* 63:827-834.
Cihil, et al. "Disabled-2 protein facilitates assembly polypeptide-2-independent recruitment of cystic fibrosis transmembrane conductance regulator to endocytic vesicles in polarized human airway epithelial cells" (2012) *J. Biol. Chem.* 287:15087-99.

(Continued)

*Primary Examiner* — Jeffrey E. Russel
(74) *Attorney, Agent, or Firm* — Licata & Tyrrell P.C.

(57) ABSTRACT

Compositions and kits including an agent that inhibits the interaction between Disabled-2 and mutant CFTR proteins, optionally in combination with a CFTR corrector, CFTR potentiator, CAL inhibitor, mucolytic, anti-inflammatory agent or a combination thereof are provided as are methods for preventing or treating cystic fibrosis.

14 Claims, 1 Drawing Sheet
Specification includes a Sequence Listing.

(56) References Cited

OTHER PUBLICATIONS

Collaco, et al. "Alpha-AP-2 directs myosin VI-dependent endocytosis of cystic fibrosis transmembrane conductance regulator chloride channels in the intestine" (2011) *J. Biol. Chem.* 285:17177-17187.
Cushing, et al. "A stabilizing influence: CAL PDZ inhibition extends the half-life of ΔF508-CFTR" (2010) *Agnew Chem. Int. Ed. Engl.* 49:9907-9911.
Dalemans, et al. "Altered chloride ion channel kinetics associated with the delta F508 cystic fibrosis mutation" (1991) Nature 354:526-528.
Dasenbrook, et al. "Persistent methicillin-resistant *Staphylococcus aureus* and rate of FEV1 decline in cystic fibrosis" (2008) *Am. J. Respir. Crit. Care Med.* 178:814-821.
Denning, et al. "Processing of mutant cystic fibrosis transmembrane conductance regulator is temperature-sensitive" (1992) *Nature* 358:761-764.
Drumm, et al. "Chloride conductance expressed by delta F508 and other mutant CFTRs in Xenopus oocytes" (1991) *Science* 254:1797-1799.
Flume, et al. "Ivacaftor in subjects with cystic fibrosis who are homozygous for the F508del-CFTR mutation" (2012) *Chest* 142:718-724.
Fu, et al. "Dab2 is a key regulator of endocytosis and post-endocytic trafficking of the cystic fibrosis transmembrane conductance regulator" (2011) *Biochem. J.* 441:633-643.
Guggino & Stanton "New insights into cystic fibrosis: molecular switches that regulate CFTR" (2006) *Nat. Rev. Mol. Cell. Biol.* 7(6):426-436.
Howard, et al. "Forskolin-induced apical membrane insertion of virally expressed, epitope-tagged CFTR in polarized MDCK cells (2002)" *Am. J. Physiol. Cell Physiol.* 279:C375-C382).
Hu, et al. "Multiple endocytic signals in the C-terminal tail of the cystic fibrosis transmembrane conductance regulator" (2002) *Biochem. J.* 354:561-72.
Kerem, et al. "Identification of the Cystic Fibrosis Gene: Genetic Analysis" (1989) *Science* 245: 1073-1080.
Lukacs, et al. "The delta F508 mutation decreases the stability of cystic fibrosis transmembrane conductance regulator in the plasma membrane. Determination of functional half-lives on transfected cells" (1993) *J. Biol. Chem.* 268:21592-21598.
Lukacs, et al. "Constitutive internalization of cystic fibrosis transmembrane conductance regulator occurs via clathrin-dependent endocytosis and is regulated by protein phosphorylation" (1997) *Biochem. J.* 328:353-361.
Motley, et al. "Clathrin-mediated endocytosis in AP-2-depleted cells" (2003) *J. Cell Biol.* 162:909-918.
Okiyoneda & Lukacs "Cell surface dynamics of CFTR: the ins and outs" (2007) *Biochim. Biophys. Acta* 1773:476-479.
Pedemonte, et al. "Small-molecule correctors of defective DeltaF508-CFTR cellular processing identified by high-throughput screening" (2005) *J. Clin. Invest.* 115:2564).
Prince, et al. "Efficient endocytosis of the cystic fibrosis transmembrane conductance regulator requires a tyrosine-based signal" (1999) *J. Biol. Chem.* 274:3602-3609.
Que, et al. "Improving rate of decline of FEV1 in young adults with cystic fibrosis" (2006) *Thorax* 61:155-157).
Ramsey, et al. "A CFTR potentiator in patients with cystic fibrosis and the G551D mutation" (2011) *N. Engl. J. Med.* 365:1663-72.
Riordan, et al. "Identification of the cystic fibrosis gene: cloning and characterization of complementary DNA" (1989) *Science* 245:1066-1173.
Riordan "CFTR function and prospects for therapy" (2008) *Annu. Rev. Biochem.* 77:701-726.
Rommens, et al. "Identification of the Cystic Fibrosis Gene: Chromosome Walking & Jumping" (1989) *Science* 245(4922):1059-1065.
Sharma, et al. "Misfolding diverts CFTR from recycling to degradation: quality control at early endosomes" (2004) *J. Cell Bio.* 164:923-933.
Swiatecka-Urban, et al. "Myosin VI regulates endocytosis of the cystic fibrosis transmembrane conductance regulator" (2004) *J. Biol. Chem.* 279:38025-31).
Swiatecka-Urban, et al. "The short apical membrane half-life of rescued {Delta}F508-cystic fibrosis transmembrane conductance regulator (CFTR) results from accelerated endocytosis of {Delta}F508-CFTR in polarized human airway epithelial cells" (2005) *J. Biol. Chem.* 280:36762-36772.
Tarran, et al. "Regulation of normal and cystic fibrosis airway surface liquid volume by phasic shear stress" (2006) *Annu. Rev. Physiol.* 68:543-61.
Taylor-Robinson, et al. "Understanding the natural progression in %FEV1 decline in patients with cystic fibrosis: a longitudinal study" (2012) *Thorax* 67:860-866.
Traub "Sorting it out: AP-2 and alternate clathrin adaptors in endocytic cargo selection" (2003) *J. Cell Biol.* 163:203-208.
Van Goor, et al. "VX-809, a CFTR Corrector, Increases the Cell Surface Density of Functional F508DEL-CFTR in Pre-clinical Models of Cystic Fibrosis" (2009) *Pediatr. Pulmonol.* 44:S154-S155.
Van Goor, et al. "Correction of the F508del-CFTR protein processing defect in vitro by the investigational drug VX-809" (2011) *Proc. Natl. Acad. Sci. USA* 108:18843-18848.
Weixel & Bradbury "Mu 2 binding directs the cystic fibrosis transmembrane conductance regulator to the clathrin-mediated endocytic pathway" (2002) *J. Biol. Chem.* 276:46251-46259.
Ye, et al. "c-Cbl facilitates endocytosis and lysosomal degradation of cystic fibrosis transmembrane conductance regulator in human airway epithelial cells" (2010) *J. Biol. Chem.* 285:27008-27018.
International Preliminary Examination Report in PCT/US 15/60071 dated May 16, 2017.
International Search Report and Written Opinion in PCT/US 15/60071 dated Mar. 31, 2016.

* cited by examiner

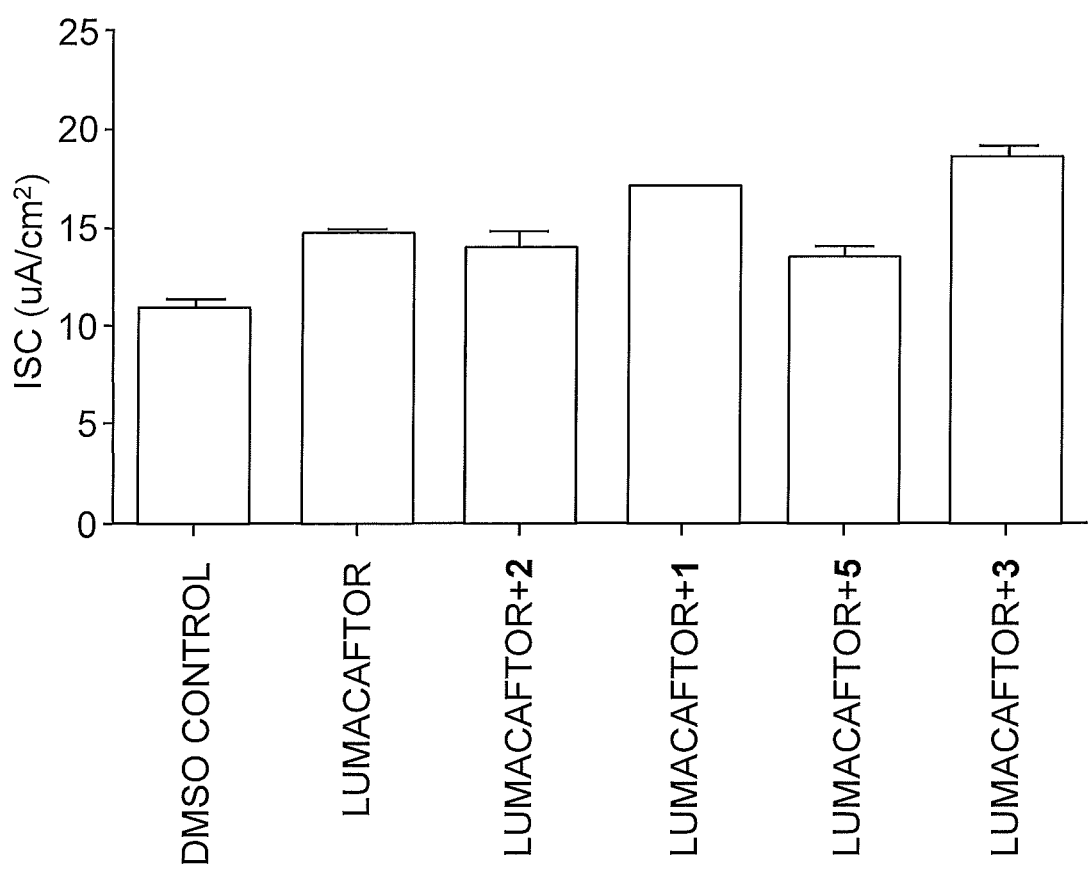

DAB2 INHIBITORS FOR THE PREVENTION AND TREATMENT OF CYSTIC FIBROSIS

This patent application is a U.S. National Stage Application of PCT/US2015/060071 filed Nov. 11, 2015 which claims the benefit of priority from U.S. Provisional Patent Application Ser. No. 62/078,499 filed Nov. 12, 2014, the teachings of each of which are herein incorporated by reference in their entirety.

BACKGROUND

The cystic fibrosis transmembrane conductance regulator (CFTR) belongs to the family of ATP binding cassette (ABC) transporters, but forms a cAMP-activated Cl⁻ channel that mediates transepithelial Cl⁻ secretion in various fluid-transporting epithelia (Riordan, et al. (1989) *Science* 245:1066-1173; Rommens, et al. (1989) *Science* 245(4922): 1059-1065; Howard, et al. (2002) *Am. J. Physiol. Cell Physiol.* 279:C375-C382). In the airway, CFTR plays a critical role in regulating mucociliary clearance by maintaining the airway surface liquid (Boucher (2004) *Eur. Respir. J.* 23:146-158; Tarran, et al. (2006) *Annu. Rev. Physiol.* 285:C1-18). CFTR-mediated Cl⁻ secretion across polarized epithelial cells is modulated at the level of both channel activity and abundance in the plasma membrane (Bertrand, et al. (2003) *Am. J. Physiol. Cell Physiol.* 285 (1):C1-18; Guggino & Stanton (2006) *Nat. Rev. Mol. Cell. Biol.* 7(6):426-436). The plasma membrane abundance of CFTR depends on its biosynthetic processing and post-maturational trafficking (Riordan (2008) *Annu. Rev. Biochem.* 77:701-726). The long plasma membrane stability of CFTR stands in contrast to its inefficient biosynthetic processing and depends primarily on efficient recycling to compensate for rapid endocytosis, which occurs in clathrin-coated vesicles (CCV) (Lukacs, et al. (1997) *Biochem. J.* 328:353-361; Prince, et al. (1999) *J. Biol. Chem.* 274:3602-3369).

In addition to defective processing, post-maturational trafficking is also critically affected by the most common disease-associated mutation in the CFTR gene. In 70% of patient alleles, loss of Phe508 (ΔF508) leads to a temperature sensitive processing defect in the CFTR protein (Riordan (2008) *Annu. Rev. Biochem.* 77:701-726). The temperature-rescued ΔF508-CFTR is partially functional as a Cl⁻ channel but it is unstable in the plasma membrane due to altered endocytic trafficking (Sharma, et al. (2004) *J. Cell Bio.* 164:923-933; Swiatecka-Urban, et al. (2005) *J. Biol. Chem.* 280:36762-36772).

Complex protein networks control the post-maturational trafficking of CFTR, which involves endocytic uptake followed either by recycling to the plasma membrane or by lysosomal degradation (Guggino & Stanton (2006) *Nat. Rev. Mol. Cell. Biol.* 7(6):426-436). Studies have shown that the plasma membrane half-life and cell-surface abundance of CFTR can be stabilized by inhibition of the CFTR-associated ligand CAL or by depletion of the ubiquitin ligase c-Cbl (Cushing, et al. (2010) *Agnew Chem. Int. Ed. Engl.* 49:9907-9911; Ye, et al. (2010) *J. Biol. Chem.* 285:27008-27018). While several proteins involved in the uptake process have been identified (Okiyoneda & Lukacs (2007) *Biochim. Biophys. Acta* 1773:476-479), their roles are incompletely defined in polarized airway epithelial cells.

Clathrin-mediated endocytic uptake requires two closely related, but distinct processes. The first involves the assembly of the clathrin coat and the second requires recruitment of cargo proteins to the site of endocytosis for incorporation into CCVs. The assembly polypeptide-2 (AP-2), a heterotetrameric complex of α, β2, σ2, and μ2 adaptins, is the prototypical endocytic adaptor with key roles in both processes (Traub (2003) *J. Cell Biol.* 163:203-208). Three of the AP-2 adaptins (α, β2, and σ2) participate directly in clathrin coat assembly. The μ2 adaptin binds directly to the YxxΦ motifs in transmembrane cargo proteins. As a result, depletion of AP-2 by more than 90% results in a 10-fold reduction of CCV number. This profoundly inhibits the endocytic uptake of cargo proteins that rely entirely on the YxxΦ motif, such as the transferrin receptor (TfR), but has very little effect on the uptake of other clathrin cargo proteins, such as the Low Density Lipoprotein Receptor (LDLR) (Motley, et al. (2003) *J. Cell Biol.* 162:909-918). Alternative adaptor proteins mediate privileged cargo recruitment independent of μ2, enabling proteins such as LDLR to maintain efficient internalization even when the number of CCVs is strongly depleted (Motley, et al. (2003) *J. Cell Biol.* 162: 909-918).

AP-2 has been shown to play a role in CFTR endocytosis in cells that endogenously express the channel (Ye, et al. (2010) *J. Biol. Chem.* 285:27008-27018; Callaco, et al. (2011) *J. Biol. Chem.* 285:17177-17187; Fu, et al. (2011) *Biochem. J.* 441:633-643). In non-epithelial cells, AP-2 is necessary for efficient CFTR endocytosis, and the μ2 adaptin interacts directly with CFTR in vitro (Prince, et al. (1999) *J. Biol. Chem.* 274:3602-3609; Weixel & Bradbury (2002) *J. Biol. Chem.* 275:3655-3660; Weixel & Bradbury (2002) *J. Biol. Chem.* 276:46251-46259). Thus, in HEK293 cells, even a modest 64% knockdown of α-AP-2 causes a 2-fold reduction in the endocytic uptake of CFTR (Collaco, et al. (2011) *J. Biol. Chem.* 285:17177-17187). In comparison, the situation in airway epithelial cells is less clear. The μ2 knockdown by more than 90% results in only a 2-fold reduction in CFTR endocytosis, compared to the dramatic reduction seen for purely YxxΦ-mediated uptake (Motley, et al. (2003) *J. Cell. Biol.* 162:909-18; Fu, et al. (2011) *Biochem. J.* 441:633-43). Furthermore, several distinct endocytic motifs have been found in the C-terminal tail of CFTR (Hu, et al. (2002) *Biochem. J.* 354:561-72), suggesting that AP-2 may not be obligatory for CFTR recruitment to CCVs in airway epithelia.

Disabled-2 (Dab2) is a clathrin-associated sorting protein (CLASP) that, like AP-2, facilitates endocytosis by organizing clathrin assembly and by recruiting cargo and other adaptor proteins (Traub (2003) *J. Cell. Biol.* 163:203-8). The Dab2 DAB homology (DH) domain binds to the plasma membrane PtdIns(4,5)P₂, while the Dab2 NPF sequence repeats assist in clathrin assembly. Moreover, the DH domain binds cargo proteins containing the Asn-Pro-Xaa-Tyr (SEQ ID NO:1) motif. Thus, Dab2 can sustain endocytosis of Asn-Pro-Xaa-Tyr (SEQ ID NO:1)-containing proteins, such as LDLR, even when CCV number is limiting (Motley, et al. (2003) *J. Cell. Biol.* 162:909-18). Dab2 can also promote endocytosis by binding directly via its DPF domain to the α adaptin and working in concert with AP-2.

Dab2 has also been implicated in CFTR endocytosis. CFTR co-immunoprecipitated with Dab2 and myosin VI in human airway epithelial cells (Swiatecka-Urban, et al. (2004) *J. Biol. Chem.* 279:38025-31), and co-localized with Dab2, AP-2 and myosin VI in rat enterocytes (Collaco, et al. (2011) *J. Biol. Chem.* 285:17177-87). CFTR abundance was increased in the intestines of Dab2 KO mice and CFTR endocytosis was inhibited after Dab2 depletion in human airway epithelial cells (Collaco, et al. (2011) *J. Biol. Chem.* 285:17177-87; Fu, et al. (2011) *Biochem. J.* 441:633-43). CFTR does not contain a canonical Asn-Pro-Xaa-Tyr (SEQ ID NO:1) motif and it has thus been proposed that its role is dependent on interactions with AP-2 and/or other endocytic adaptors, such as myosin VI (Collaco, et al. (2011) *J. Biol. Chem.* 285:17177-87; Fu, et al. (2011) *Biochem. J.* 441:633-43). In this respect, it has been shown that in polarized human airway epithelial cells (CFBE41o-), Dab2 recruits CFTR to CCVs and mediates CFTR endocytosis by an AP-2-independent mechanism that requires the Dab2 DH domain (Cihil, et al. (2012) *J. Biol. Chem.* 287:15087-99).

Current treatments for cystic fibrosis generally focus on controlling infection through antibiotic therapy and promoting mucus clearance by use of postural drainage and chest percussion. However, even with such treatments, frequent hospitalization is often required as the disease progresses. New therapies designed to increase chloride ion conductance in airway epithelial cells have been proposed, and restoration of the expression of functional CFTR at the cell surface is considered a major therapeutic goal in the treatment of cystic fibrosis, a disease that affects ~30,000 patients in the U.S., and ~70,000 patients worldwide. For example, KALYDECO (Ivacaftor; VX-770) is an FDA-approved compound that 'potentiates' the open probability (Po) of CFTR channels, including the G551D mutant, and thus ameliorates the underlying molecular lesion in this group of patients. A 48-week clinical trial showed excellent efficacy, including a 10.6% improvement in lung function (predicted forced expiratory volume in 1 second; FEV1), a 55% drop in pulmonary exacerbations, and a 48 mEq/L reduction in sweat chloride (Ramsey, et al. (2011) *N. Engl. J. Med.* 365:1663-72). While showing efficacy in subjects with the G551D mutation, KALYDECO is not useful as a monotherapy for the largest group of CF patients. In ~70% of mutant alleles, Phe508 is deleted (ΔF508; Kerem, et al. (1989) *Science* 245: 1073-1080). As a result, ~50% of CF patients are ΔF508 homozygous and ~40% are heterozygous. Unfortunately, clinical trials in ΔF508 homozygotes show low efficacy for KALYDECO alone (Flume, et al. (2012) *Chest* 142:718-724).

In the absence of interventions, ΔF508-CFTR exhibits three defects: folding, gating, and stability (Riordan (2008) *Annu. Rev. Biochem.* 77:701-726; Cheng, et al. (1990) *Cell* 63:827-834; Lukacs, et al. (1993) *J. Biol. Chem.* 268:21592-21598; Dalemans, et al. (1991) *Nature* 354:526-528). However, if folding is restored, ΔF508-CFTR retains some channel activity (Drumm, et al. (1991) *Science* 254:1797-1799; Denning, et al. (1992) *Nature* 358:761-764). 'Corrector' compounds have been identified such as corr-4a (Pedemonte, et al. (2005) *J. Clin. Invest.* 115:2564) and Lumacaftor (VX-809), which partially alleviate the folding defect and allows some ΔF508-CFTR to reach the apical membrane (Van Goor, et al. (2009) *Pediatr. Pulmonol.* 44:S154-S155; Van Goor, et al. (2011) *Proc. Natl. Acad. Sci. USA* 108:18843-18848). Although Lumacaftor yields only limited benefits in monotherapy, it shows greater efficacy in combination with KALYDECO: 25% of patients showed a >10% increase in FEV1 and 55% of patients showed >5% increase, with few adverse effects. While a 5% or 10% improvement is clinically meaningful, FEV1 drops approximately 1-2% per year in CF patients (Dasenbrook, et al. (2008) *Am. J. Respir. Crit. Care Med.* 178:814-821; Que, et al. (2006) *Thorax* 61:155-157), even in the absence of acceleration by pulmonary exacerbations (Taylor-Robinson, et al. (2012) *Thorax* 67:860-866). Thus, further improvements are required, especially for non-responders and the 40% of ΔF508-CFTR heterozygous patients.

SUMMARY OF THE INVENTION

This invention provides compositions for inhibiting the interaction between a degradation-prone CFTR and Dab2 and methods for using the same for preventing or treating cystic fibrosis. In one embodiment, the composition is a peptide having the amino acid sequence of SEQ ID NO:2, or a derivative or peptidomimetic thereof. In some embodiments, the peptide is set forth in Table 1. In other embodiments, the peptide is derivatized with a label, one or more post-translational modifications, a cell-penetrating sequence, or a combination thereof. A pharmaceutical composition containing the peptide is also provided, wherein said composition may be formulated for administration via inhalation and/or optionally include a CFTR corrector, CFTR potentiator, CAL inhibitor, mucolytic, anti-inflammatory agent or a combination thereof.

In another embodiment, the composition is a compound of Formula I, II or III or hydrate, prodrug or pharmaceutically acceptable salt thereof, preferably in a pharmaceutical composition, which may be formulated for administration via inhalation and/or optionally include a CFTR corrector, CFTR potentiator, CAL inhibitor, mucolytic, anti-inflammatory agent or a combination thereof.

This invention also provides a kit containing (a) an agent that inhibits the interaction between a degradation-prone CFTR and Dab2; and (b) a CFTR corrector, CFTR potentiator, CAL inhibitor, mucolytic, anti-inflammatory agent or a combination thereof. In some embodiments, the agent is a peptide having the amino acid sequence of SEQ ID NO:2 (e.g., as listed in Table 1), or a derivative or peptidomimetic thereof. In other embodiments, the agent is a compound of Formula I, II or III, or hydrate, prodrug or pharmaceutically acceptable salt thereof.

Methods for preventing or treating cystic fibrosis by administering to a subject in need of treatment a pharmaceutical composition containing a peptide or compound of Formula I, II or III, either alone or in combination with a CFTR corrector, CFTR potentiator, CAL inhibitor mucolytic, anti-inflammatory agent is also provided.

BRIEF DESCRIPTION OF THE DRAWINGS

FIG. 1 shows the Isc (short-circuit current) of CFBE airway epithelial cells expressing the disease-associated ΔF508-CFTR mutant and treated with Lumacaftor (0.1 µM) or Lumacaftor in combination with Dab2 inhibitors, 1, 2, 3 and 5 (20 µM).

DETAILED DESCRIPTION OF THE INVENTION

Novel inhibitors have now been identified that block the interaction or binding of CFTR with the Dab2 by competitive displacement. By inhibiting this interaction with Dab2, degradation-prone CFTR proteins are stabilized and successfully transported to the cell surface. Representative peptide and peptidomimetic Dab2 inhibitors were shown to increase the apical cell-surface expression and transepithelial chloride efflux of the most common CFTR mutation associated with CF. Accordingly, inhibitors of the present invention find application in increasing the cell surface expression of degradation-prone CFTR proteins and in the treatment for CF. In particular, Dab2 inhibition is of use in combination therapies for reversing the ΔF508 stability defect.

As used herein, "cell surface expression" of a CFTR protein refers to CFTR protein which has been transported to the surface of a cell. In this regard, an agent that increases the cell surface expression of a CFTR protein refers to an agent that increases the amount of CFTR protein, which is present or detected at the plasma membrane of a cell, as compared to a cell which is not contacted with the agent.

Genetic, biochemical, and cell biological studies have revealed a complex network of protein-protein interactions that are required for correct CFTR trafficking, including a number of PDZ (PSD-95, discs-large, zonula occludens-1) proteins, which act as adaptor molecules, coupling CFTR to other components of the trafficking and localization machinery, and to other transmembrane channels and receptors (Kunzelmann (2001) *News Physiol. Sci.* 16:167-170; Guggino & Stanton (2006) *Nat. Rev. Mol. Cell Biol.* 7:426-436). Class I PDZ domains typically recognize C-terminal binding motifs characterized by the sequence -(Ser/Thr)-X-Φ-COOH (where Φ represents a hydrophobic side chain, and X represents any amino acid) (Harris & Lim (2001) *J. Cell Sci.* 114:3219-3231; Drône & Eggermont (2005) *Am. J. Physiol.* 288:C20-C29). The cytoplasmic C-terminus of CFTR satisfies the class I PDZ binding motif, ending in the sequence -Thr-Arg-Leu (Hall, et al. (1998) *Proc. Natl. Acad. Sci. USA* 95:8496-8501; Short, et al. (1998) *J. Biol. Chem.* 273:19797-19801; Wang, et al. (1998) *FEBS Lett.* 427:103-108) and it has been demonstrated that CFTR C-terminal PDZ-binding motif controls retention of the protein at the apical membrane and modulates its endocytic recycling (Moyer, et al. (2000) *J. Biol. Chem.* 275:27069-27074; Swiatecka-Urban, et al. (2002) *J. Biol. Chem.* 277:40099-40105). PDZ proteins that have been shown to bind or interact with CFTR include NHERF1 (Na+/H+ exchanger regulatory factor 1; also known as EBP50), NHERF2 (Na+/H+ exchanger regulatory factor 2, also known as E3KARP), NHERF3 (Na+/H+ exchanger regulatory factor 3, also known as CAP70, PDZK1, or NaPi CAP-1), NHERF4 (Na+/H+ exchanger regulatory factor 4, also known as IKEPP or NaPi CAP-2), and CAL (CFTR-associated ligand; also known as PIST, GOPC, and FIG) (Guggino & Stanton (2006) supra; Li & Naren (2005) *Pharmacol. Ther.* 108:208-223). In this respect, in certain embodiments, a selective inhibitor of this invention does not bind to interact with NHERF1, NHERF2, NHERF3, NHERF4 or CAL.

Dab2 is a clathrin associated sorting protein that acts as an endocytic adaptor by interacting with sequence motifs on target proteins, adaptor proteins (AP-2, FCHO2) (Mulkearns & Cooper (2012) *Mol. Biol. Cell* 23:1330-1342; Mishra, et al. (2004) *J. Biol. Chem.* 279:46191-203), clathrin, and motor proteins (myosin VI). Dab2 binds to target proteins via an amino-terminal region (Dab-homology (DH) domain) of ~150 amino acids that acts as a protein-protein and protein-phospholipid binding module (Yun, et al. (2003) *J. Biol. Chem.* 278:36572-81). The DH domain of Dab-family members was originally characterized as a phosphotyrosine binding (PTB) domain until the discovery that the DH domain binds more tightly to non-phosphorylated tyrosine target sequence (Howell, et al. (1999) *Mol. Cell. Biol.* 19:5179-88). Dab2-DH has a hydrophobic pocket (residues: F166, K163, V159, I124, R126) that accommodates and preferentially binds to non-bulky aromatic residues such as Tyr/Phe at P$^{-5}$ while bulkier residues such as Trp are not tolerated (Yun, et al. (2003) *J. Biol. Chem.* 278:36572-81; Howell, et al. (1999) *Mol. Cell. Biol.* 19:5179-88). The Asn-Pro-Xaa-Tyr (SEQ ID NO:1) motif provides a type I β turn, which positions the Tyr$^0$ in a polar pocket where most of the binding energy is concentrated. The data herein indicates that molecules that bind the Dab2-DH hydrophobic pocket disrupt the interaction of Dab2 with CFTR thereby stabilizing mutant CFTR protein and facilitating cell surface expression of the same.

The CFTR protein and mutants thereof are well-known in the art and wild-type human CFTR is disclosed in GENBANK Accession No. NP_000483, incorporated herein by reference. Misfolding of mutant CFTR proteins has been shown to dramatically augment the ubiquitination susceptibility of the protein in post-Golgi compartments (Swiatecka-Urban, et al. (2005) *J. Biol. Chem.* 280:36762). Thus, for the purposes of the present invention, the term "degradation-prone" when used as a modifier of a CFTR protein, refers to a mutant CFTR protein that exhibits an increased rate of degradation following initial trafficking to the cell surface and a decrease in the amount of CFTR protein present at the cell surface (i.e., plasma membrane). Examples of degradation-prone CFTR proteins include, but are not limited to ΔF508 CFTR and A70F CFTR (see Sharma, et al. (2004) *J. Cell Biol.* 164:923). Other degradation-prone CFTR proteins are known in the art and/or can be identified by routine experimentation. For example, the rate or amount of transport of CFTR protein from the cell surface can be determined by detecting the amount of complex-glycosylated CFTR protein present at the cell surface, in endoplasmic vesicles and/or in lysosomes using methods such as cell surface immunoprecipitation or biotinylation or cell immunocytochemistry with an antibody specific for CFTR protein. Additional methods, both in vivo and in vitro, are known in the art that can be used for detecting an increase or decrease in cell surface expression of a CFTR protein.

Particular embodiments of this invention embrace inhibitory agents that selectively block the interaction or binding between a degradation-prone CFTR and Dab2. As used herein, a "selective inhibitor of the CFTR and Dab2 interaction" or "an agent that selectively inhibits the interaction between the degradation-prone CFTR and Dab2" is any molecular species that is an inhibitor of the CFTR and Dab2 interaction but which fails to inhibit, or inhibits to a substantially lesser degree the interaction between CFTR and proteins that stabilize degradation-prone CFTR, e.g., NHERF1 and NHERF2. Methods for assessing the selectively of an inhibitor of the CFTR and Dab2 interaction are disclosed herein and can be carried out in in vitro or in vivo assays.

As indicated, the present invention features compositions and methods for facilitating the cell surface expression of mutant CFTR by selectively blocking the interaction between a degradation-prone CFTR and Dab2. Agents of the present invention can be any molecular species, with particular embodiments embracing peptides, peptide mimetics and small organic molecules.

As used herein, the term "peptide" denotes an amino acid polymer that is composed of at least two amino acids covalently linked by an amide bond. Peptides of the present invention are desirably 10 to 20 residues in length, or more desirably 15 to 20 residues in length. In certain embodiments, a selective inhibitor of the CFTR and Dab2 interaction is a 15 to 20 residue peptide containing the amino acid sequence Gln-Asn-Gly-Phe-Asp-Asn-Pro-Xaa$_1$-Xaa$_2$-Tyr-Xaa$_3$-Xaa$_4$-Xaa$_5$-Glu-Xaa$_6$-Met-Gln-Xaa$_7$ (SEQ ID NO:2), wherein Xaa$_1$ is Asn or His; Xaa$_2$ is present or absent and when present is Pro; Xaa$_3$ is Val, Leu, Phe, Glu, Asp, Gln, Asn, or His; Xaa$_4$ is Pro or Phe; Xaa$_5$ is Phe or Gln; Xaa$_6$ is Ser, Thr, Asn or Gln; Xaa$_7$ is Asn or Ala. In certain embodiments of the present invention, a selective inhibitor of the CFTR and Dab2 interaction is a peptide having an amino acid sequence as listed in Table 1.

TABLE 1

| Peptide ID | Peptide Sequence | SEQ ID NO: |
|---|---|---|
| STA01 | QNGFDNPNYQFFEQMQN | 3 |
| STA02 | QNGFDNPNPYQPQENMQA | 4 |

In accordance with the present invention, derivatives of the peptides of the invention are also provided. As used herein, a peptide derivative is a molecule which retains the primary amino acids of the peptide, however, the N-terminus, C-terminus, and/or one or more of the side chains of the amino acids therein have been chemically altered or derivatized. Such derivatized peptides include, for example, naturally occurring amino acid derivatives, for example, 4-hydroxyproline for proline, 5-hydroxylysine for lysine, homoserine for serine, ornithine for lysine, and the like. Other derivatives or modifications include, e.g., a label, such as fluorescein or tetramethylrhodamine; or one or more post-translational modifications such as acetylation, amidation, formylation, hydroxylation, methylation, phosphorylation, sulfatation, glycosylation, or lipidation. Indeed, certain chemical modifications, in particular N-terminal glycosylation, have been shown to increase the stability of peptides in human serum (Powell et al. (1993) *Pharma. Res.* 10:1268-1273). Peptide derivatives also include those with increased membrane permeability obtained by N-myristoylation (Brand, et al. (1996) *Am. J. Physiol. Cell. Physiol.* 270:C1362-C1369).

In addition, a peptide derivative of the invention can include a cell-penetrating sequence which facilitates, enhances, or increases the transmembrane transport or intracellular delivery of the peptide into a cell. For example, a variety of proteins, including the HIV-1 Tat transcription factor, *Drosophila* Antennapedia transcription factor, as well as the herpes simplex virus VP22 protein have been shown to facilitate transport of proteins into the cell (Wadia and Dowdy (2002) *Curr. Opin. Biotechnol.* 13:52-56). Further, an arginine-rich peptide (Futaki (2002) *Int. J. Pharm.* 245: 1-7), a polylysine peptide containing Tat PTD (Hashida, et al. (2004) *Br. J. Cancer* 90(6):1252-8), Pep-1 (Deshayes, et al. (2004) *Biochemistry* 43(6):1449-57) or an HSP70 protein or fragment thereof (WO 00/31113) is suitable for enhancing intracellular delivery of a peptide or peptidomimetic of the invention into the cell. Examples of known cell-penetrating peptides (CPP) are provided in Table 2.

TABLE 2

| CPP | Sequence | SEQ ID NO: |
|---|---|---|
| MPG | GALFLGFLGAAGSTMGAWSQPKKKRKV | 5 |
| R8 | RRRRRRRR | 6 |
| Tat (48-60) | GRKKRRQRRRPPQQ | 7 |
| Transportan | GWTLNSAGYLLGKINLKALAALAKKIL | 8 |
| TP10 | AGYLLGKINLKALAALAKKIL | 9 |
| MAP | KLALKLALKALKAALKLA | 10 |
| MPG-a | GALFLAFLAAALSLMGLWSQPKKKRKV | 11 |
| Penetratin | RQIKIWFQNRRMKWKK | 12 |

While a peptide of the invention can be derivatized with by one of the above indicated modifications, it is understood that a peptide of this invention may contain more than one of the above described modifications within the same peptide.

The present invention also encompasses peptidomimetics of the peptides disclosed herein. Peptidomimetics refer to a synthetic chemical compound which has substantially the same structural and/or functional characteristics of the peptides of the invention. The mimetic can be entirely composed of synthetic, non-natural amino acid analogues, or can be a chimeric molecule including one or more natural peptide amino acids and one or more non-natural amino acid analogs. The mimetic can also incorporate any number of natural amino acid conservative substitutions as long as such substitutions do not destroy the activity of the mimetic. Routine testing can be used to determine whether a mimetic has the requisite activity, e.g., that it can inhibit the interaction between CFTR and Dab2. The phrase "substantially the same," when used in reference to a mimetic or peptidomimetic, means that the mimetic or peptidomimetic has one or more activities or functions of the referenced molecule, e.g., selective inhibition of the Dab2 and CFTR interaction.

There are clear advantages for using a mimetic of a given peptide. For example, there are considerable cost savings and improved patient compliance associated with peptidomimetics, since they can be administered orally compared with parenteral administration for peptides. Furthermore, peptidomimetics are much cheaper to produce than peptides.

Thus, peptides described above have utility in the development of such small chemical compounds with similar biological activities and therefore with similar therapeutic utilities. The techniques of developing peptidomimetics are conventional. For example, peptide bonds can be replaced by non-peptide bonds or non-natural amino acids that allow the peptidomimetic to adopt a similar structure, and therefore biological activity, to the original peptide. Further modifications can also be made by replacing chemical groups of the amino acids with other chemical groups of similar structure. The development of peptidomimetics can be aided by determining the tertiary structure of the original peptide, either free or bound to a Dab2 protein, by NMR spectroscopy, crystallography and/or computer-aided molecular modeling. These techniques aid in the development of novel compositions of higher potency and/or greater bioavailability and/or greater stability than the original peptide (Dean (1994) *BioEssays* 16:683-687; Cohen & Shatzmiller (1993) *J. Mol. Graph.* 11:166-173; Wiley & Rich (1993) *Med. Res. Rev.* 13:327-384; Moore (1994) *Trends Pharmacol. Sci.* 15:124-129; Hruby (1993) *Biopolymers* 33:1073-1082; Bugg, et al. (1993) *Sci. Am.* 269:92-98). Once a potential peptidomimetic compound is identified, it may be synthesized and assayed using an assay described herein or any other appropriate assay for monitoring cell surface expression of CFTR.

It will be readily apparent to one skilled in the art that a peptidomimetic can be generated from any of the peptides described herein. It will furthermore be apparent that the peptidomimetics of this invention can be further used for the development of even more potent non-peptidic compounds, in addition to their utility as therapeutic compounds.

Peptide mimetic compositions can contain any combination of non-natural structural components, which are typically from three structural groups: residue linkage groups other than the natural amide bond ("peptide bond") linkages; non-natural residues in place of naturally occurring amino acid residues; residues which induce secondary structural mimicry, i.e., induce or stabilize a secondary structure, e.g., a beta turn, gamma turn, beta sheet, alpha helix conformation, and the like; or other changes which confer resistance to proteolysis. For example, a polypeptide can be characterized as a mimetic when one or more of the residues are joined by chemical means other than an amide bond. Individual peptidomimetic residues can be joined by amide bonds, non-natural and non-amide chemical bonds other chemical bonds or coupling means including, for example, glutaraldehyde, N-hydroxysuccinimide esters, bifunctional maleimides, N,N'-dicyclohexylcarbodiimide (DCC) or N,N'-diisopropyl-carbodiimide (DIC). Linking groups alternative to the amide bond include, for example, ketomethylene (e.g., C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in *Chemistry and Biochemistry of Amino Acids, Peptides and Proteins*, 7:267-357, "Peptide and Backbone Modifications," Marcel Decker, NY).

As discussed, a peptide can be characterized as a mimetic by containing one or more non-natural residues in place of a naturally occurring amino acid residue. Non-natural residues are known in the art. Particular non-limiting examples of non-natural residues useful as mimetics of natural amino acid residues are mimetics of aromatic amino acids include, for example, D- or L-naphthylalanine; D- or L-phenylglycine; D- or L-2 thienylalanine; D- or L-1, -2, 3-, or 4-pyrenylalanine; D- or L-3-thienylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; D- or L-p-methoxy-biphenyl-phenylalanine; and D- or L-2-indole(alkyl)alanines, where alkyl can be substituted or unsubstituted methyl, ethyl, propyl, hexyl, butyl, pentyl, isopropyl, iso-butyl, sec-isotyl, iso-pentyl, or a non-acidic amino acid. Aromatic rings of a non-natural amino acid that can be used in place a natural aromatic ring include, for example, thiazolyl, thiophenyl, pyrazolyl, benzimidazolyl, naphthyl, furanyl, pyrrolyl, and pyridyl aromatic rings.

Cyclic peptides or cyclized residue side chains also decrease susceptibility of a peptide to proteolysis by exopeptidases or endopeptidases. Thus, certain embodiments embrace a peptidomimetic of the peptides disclosed herein, whereby one or more amino acid residue side chains are cyclized according to conventional methods.

Mimetics of acidic amino acids can be generated by substitution with non-carboxylate amino acids while maintaining a negative charge; (phosphono)alanine; and sulfated threonine. Carboxyl side groups (e.g., aspartyl or glutamyl) can also be selectively modified by reaction with carbodiimides (R'—N=C=N—R') including, for example, 1-cyclohexyl-3(2-morpholinyl-(4-ethyl) carbodiimide or 1-ethyl-3 (4-azonia-4,4-dimetholpentyl) carbodiimide. Aspartyl or glutamyl groups can also be converted to asparaginyl and glutaminyl groups by reaction with ammonium ions.

Lysine mimetics can be generated (and amino terminal residues can be altered) by reacting lysinyl with succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4-pentanedione, and transamidase-catalyzed reactions with glyoxylate.

Methionine mimetics can be generated by reaction with methionine sulfoxide. Proline mimetics of include, for example, pipecolic acid, thiazolidine carboxylic acid, dehydroproline, 3- or 4-methylproline, and 3,3-dimethylproline.

One or more residues can also be replaced by an amino acid (or peptidomimetic residue) of the opposite chirality. Thus, any amino acid naturally occurring in the L-configuration (which can also be referred to as R or S, depending upon the structure of the chemical entity) can be replaced with the same amino acid or a mimetic, but of the opposite chirality, referred to as the D-amino acid, but which can additionally be referred to as the R- or S-form.

As will be appreciated by one skilled in the art, the peptidomimetics of the present invention can also include one or more of the modifications described herein for derivatized peptides, e.g., a label, one or more post-translational modifications, or cell-penetrating sequence.

As with peptides of the invention, peptidomimetics are desirably 10 to 20 residues in length, or more desirably 15 to residues in length. In certain embodiments, a selective inhibitor of the CFTR and Dab2 interaction is a 15 to 20 residue peptidomimetic based on the amino acid sequence of SEQ ID NO:2.

Also included with the scope of the invention are peptides and peptidomimetics that are substantially identical to a sequence set forth herein, in particular SEQ ID NO:2. The term "substantially identical," when used in reference to a peptide or peptidomimetic, means that the sequence has at least 75% or more identity to a reference sequence (e.g., 80%, 85%, 90%, 95%, 96%, 97%, 98%, 99%). The length of comparison sequences will generally be at least 5 amino acids, but typically more, at least 6 to 10, 7 to 15, or 8 to 20 residues. In one aspect, the identity is over a defined sequence region, e.g., the amino or carboxy terminal 3 to 5 residues.

The peptides, derivatives and peptidomimetics can be produced and isolated using any method known in the art. Peptides can be synthesized, whole or in part, using chemical methods known in the art (see, e.g., Caruthers (1980) *Nucleic Acids Res. Symp. Ser.* 215-223; Horn (1980) *Nucleic Acids Res. Symp. Ser.* 225-232; and Banga (1995) *Therapeutic Peptides and Proteins, Formulation, Processing and Delivery Systems*, Technomic Publishing Co., Lancaster, Pa.). Peptide synthesis can be performed using various solid-phase techniques (see, e.g., Roberge (1995) *Science* 269:202; Merrifield (1997) *Methods Enzymol.* 289:3-13) and automated synthesis may be achieved, e.g., using the ABI 431A Peptide Synthesizer (Perkin Elmer) in accordance with the manufacturer's instructions.

Individual synthetic residues and peptides incorporating mimetics can be synthesized using a variety of procedures and methodologies known in the art (see, e.g., *Organic Syntheses Collective Volumes*, Gilman, et al. (Eds) John Wiley & Sons, Inc., NY). Peptides and peptide mimetics can also be synthesized using combinatorial methodologies. Techniques for generating peptide and peptidomimetic libraries are well-known, and include, for example, multipin, tea bag, and split-couple-mix techniques (see, for example, al-Obeidi (1998) *Mol. Biotechnol.* 9:205-223; Hruby (1997) *Curr. Opin. Chem. Biol.* 1:114-119; Ostergaard (1997) *Mol. Divers.* 3:17-27; and Ostresh (1996) *Methods Enzymol.* 267:220-234). Modified peptides can be further produced by chemical modification methods (see, for example, Belousov (1997) *Nucleic Acids Res.* 25:3440-3444; Frenkel (1995) *Free Radic. Biol. Med.* 19:373-380; and Blommers (1994) *Biochemistry* 33:7886-7896).

Alternatively, peptides of this invention can be prepared in recombinant protein systems using polynucleotide sequences encoding the peptides. By way of illustration, a nucleic acid molecule encoding a peptide of the invention is introduced into a host cell, such as bacteria, yeast or mammalian cell, under conditions suitable for expression of the peptide, and the peptide is purified or isolated using methods known in the art. See, e.g., Deutscher et al. (1990) *Guide to Protein Purification: Methods in Enzymology*, Vol. 182, Academic Press.

It is contemplated that the peptides and mimetics disclosed herein can be used as lead compounds for the design and synthesis of compounds with improved efficacy, clearance, half-lives, and the like. One approach includes structure-activity relationship (SAR) analysis (e.g., NMR analysis) to determine specific binding interactions between the agent and Dab2 or CFTR to facilitate the development of more efficacious agents. Agents identified in such SAR analysis or from agent libraries can then be screened for their ability to increase cell surface expression of CFTR.

In this regard, the present invention also relates to a method for identifying an agent which facilitates cell surface expression of a degradation-prone CFTR. The method of the invention involves contacting Dab2 with a test agent under conditions allowing an interaction between the agent and Dab2, and determining whether the agent competitively displaces binding of a degradation-prone CFTR to Dab2. Particular degradation-prone CFTRs that can be used include, but are not limited to, ΔF508 and R1066C.

In one embodiment, the method is performed in vivo. Various detection methods can be employed to determine whether the agent displaces CFTR from Dab2. For example, displacement can be based on detecting an increase in an amount of CFTR protein on the cell surface, immunostaining with a specific antibody (e.g., anti-CFTR, M3A7), or direct visualization (e.g., a CFTR-GFP fusion). Additional methods useful for determining whether there is an increase in cell surface protein included cell panning. In cell panning assays, plates are coated with an antibody that binds to the cell surface protein. The number of cells that binds to the antibody coated plate corresponds to an amount of protein on the cell surface.

In another embodiment, the method is performed in vitro. In accordance with this embodiment, a combination of peptide-array screening and fluorescence polarization is used to identify agents that bind to an isolated Dab2-DH domain. By way of illustration, the high-affinity Dab2-binding peptides disclosed herein (i.e., STA01 and STA02) were used as reporters for small-molecule screening assays, wherein the small molecules competed for binding to the Dab2-DH domain. This assay identified a number of small organic molecules that inhibited the interaction between Dab2 and CFTR (see Table 5).

Accordingly, the present invention also provides small organic molecules as agents that exhibit Dab2 inhibitory activity, wherein said agents have the structure of Formula I, including hydrates, prodrugs or pharmaceutically acceptable salts thereof:

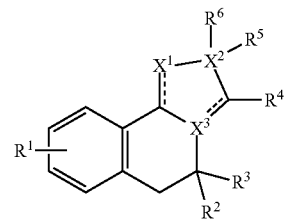

Formula I wherein
$R^1$ is present or absent, and when present is a substituent on one or more ring atoms and is for each ring atom independently a hydroxyl group, a halo group, or a substituted or unsubstituted lower alkyl or alkoxy group;
$R^2$, $R^3$, $R^5$ and $R^6$ are independently present or absent and when present independently represent hydrogen or a substituted or unsubstituted lower alkyl;
$R^4$ is hydrogen, =O or =S; or
$R^4$ together with $R^3$ or $R^5$ form a substituted or unsubstituted cycloalkyl or heterocycloalkyl group;
$X^1$ is N or C;
$X^2$ is N, C or C—C or C=C;
$X^3$ is N, C or C—$R^7$, wherein $R^7$ is a substituted or unsubstituted lower alkyl; and
dashed bonds are independently present or absent.

In certain embodiments, an agent exhibiting Dab2 inhibitory activity has the structure of Formula II, including hydrates, prodrugs or pharmaceutically acceptable salts thereof:

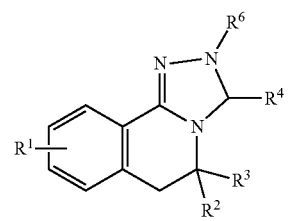

Formula II wherein
$R^1$ is present or absent, and when present is a substituent on one or more ring atoms and is for each ring atom independently a hydroxyl group, a halo group, or a substituted or unsubstituted lower alkyl or alkoxy group;
$R^2$, $R^3$ and $R^6$ are independently present or absent and when present independently represent hydrogen or a substituted or unsubstituted lower alkyl; and
$R^4$ is =O or =S.

In other embodiments, an agent exhibiting Dab2 inhibitory activity has the structure of Formula III, including hydrates, prodrugs or pharmaceutically acceptable salts thereof:

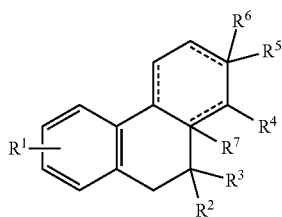

Formula III wherein

R¹ is present or absent, and when present is a substituent on one or more ring atoms and is for each ring atom independently a hydroxyl group, a halo group, or a substituted or unsubstituted lower alkyl or alkoxy group;

R², R³, R⁴, R⁵ and R⁶ are independently present or absent and when present independently represent hydrogen or a substituted or unsubstituted lower alkyl; or R⁴ together with R³ or R⁵ form a substituted or unsubstituted cycloalkyl or heterocycloalkyl group;

R⁷ is a substituted or unsubstituted lower alkyl; and dashed bonds are independently present or absent.

"Alkoxy" means a radical —OR where R is alkyl as defined herein, e.g., methoxy, ethoxy, propoxy, or 2-propoxy, n-, iso-, or tert-butoxy, and the like.

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), or pentyl (including all isomeric forms), and the like. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, and amino.

"Cycloalkyl" means a monocyclic or fused bicyclic, saturated or partially unsaturated, monovalent hydrocarbon radical of three to ten carbon ring atoms. Unless otherwise stated, the valency of the group may be located on any atom of any ring within the radical, valency rules permitting. More specifically, the term cycloalkyl includes, but is not limited to, cyclopropyl, cyclobutyl, cyclopentyl, cyclohexyl, decahydronaphthyl (including, but not limited to decahydronaphth-1-yl, decahydronaphth-2-yl, and the like), norbornyl, adamantly, or cyclohexenyl, and the like. The cycloalkyl ring is unsubstituted or may be substituted with one or more "ring system substituents" which may be the same or different, and are as defined herein.

"Halogen" or "halo" means fluorine, chlorine, bromine, or iodine. Preferred halogens are fluorine, chlorine and bromine.

"Heterocycloalkyl" means a saturated or partially unsaturated monovalent monocyclic group of 3 to 8 ring atoms or a saturated or partially unsaturated monovalent fused bicyclic group of 5 to 12 ring atoms in which one, two, or three ring atoms are heteroatoms independently selected from the group consisting of N, O, and S. Unless otherwise stated, the valency of the group may be located on any atom of any ring within the radical, valency rules permitting. More specifically the term heterocycloalkyl includes, but is not limited to, pyrrolidinyl, piperidinyl, morpholinyl, piperazinyl, homopiperazinyl, tetrahydropyranyl, 2-oxopiperidinyl, 5-oxo-4H-[1,2,4]oxadiazol-3-yl, and thiomorpholinyl, and the derivatives thereof and N-oxide or a protected derivative thereof. Unless stated otherwise, the heterocyloalkyl ring is unsubstituted or may be substituted with one, two, or three "ring system substituents" which may be the same or different, and are as defined herein.

"Ring system substituent" means a substituent attached to an aromatic or non-aromatic ring system, which, for example, replaces an available hydrogen on the ring system. Ring system substituents may be the same or different, each being independently selected from the group consisting of —C(=NH)(NH₂), —NHC(=NH) (NH₂), alkyl, alkenyl, alkynyl, alkoxy, acyl, alkylcarbonylamino, carboxy, carboxyalkyl, alkoxycarbonyl, alkoxycarbonylalkyl, cyano, nitro, alkylthio, halo, haloalkyl, haloalkoxy, amino, alkylamino, dialkylamino, aminocarbonyl, alkyl aminocarbonyl, dialkylaminocarbonyl, alkyl sulfonyl, cycloalkylsulfonyl, alkylsulfonylamino, alkylaminosulfonyl, haloalkylamino, oxo, hydroxy, hydroxyalkyl, hydroxyalkyloxy, hydroxyalkyloxyalkyl, alkoxyalkyloxyalkyl, aryl, heteroaryl, cycloalkyl, cycloalkylamino, cycloalkyloxy, heteroaralkyloxy, aminoalkyl, aminoalkyloxy, alkoxyalkyl, alkoxyalkylcarbonyl, alkoxyalkyloxy, haloalkoxyalkyl, aryloxyalkyl, heteroaryloxyalkyl, heterocycloalkyl, heterocycloalkyloxyalkyl, heterocycloalkylalkyl, heterocycloalkylalkyloxy, and heterocycloalkyloxy.

Any undefined valency on an atom of a structure shown in this application implicitly represents a hydrogen atom bonded to the atom.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

"Pharmaceutically acceptable salts" means salts of compounds of the present invention which are pharmaceutically acceptable, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and di-carboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

Compounds of the invention may also exist in prodrug form. Since prodrugs are known to enhance numerous desirable qualities of pharmaceuticals, e.g., solubility, bioavailability, manufacturing, etc., the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a patient, cleaves to form a hydroxy, amino, or carboxylic acid, respectively. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, succinates, fumarates, maleates, methylene-propionates, bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

Agents specifically disclosed herein, as well as derivatives, and peptidomimetics of said agents and agents identified by design and/or screening assays find application in increasing in the cell surface expression of degradation-prone CFTR proteins and in the treatment of CF. Thus, methods for increasing the cell surface expression of a degradation-prone CFTR and treating cystic fibrosis are also provided by this invention.

In accordance with one embodiment, the cell surface expression of a degradation-prone CFTR protein is enhanced or increased by contacting a cell expressing a degradation-prone CFTR with an agent that decreases or inhibits the interaction between the CFTR protein and Dab2 so that the cell surface expression of the CFTR protein is increased or enhanced. Desirably, the agent is administered in an amount that effectively stabilizes the degradation-prone CFTR protein and increases the amount of said CFTR protein present or detectable at the cell surface by at least 60%, 70%, 80%, 90%, 95%, 99% or 100% as compared to cells not contacted with the agent. Any cell can be employed in this method of the invention so long as it expresses a degradation-prone CFTR. Specific examples of such cells include, but are not limited to, primary cells of a subject with CF or cultured airway epithelial cell lines derived from a CF patient's bronchial epithelium (e.g., CFBE41O—). It is contemplated that this method of the invention can be used to increase cell surface expression of a degradation-prone CFTR protein in a human subject as well as increase the cell surface expression of a degradation-prone CFTR protein in an, isolated cell or cell culture to, e.g., study the transport and/or activity of the mutant protein at the cell surface.

In another embodiment, a subject with CF or at risk of CF is treated with one or more the agents of the invention. In accordance with this embodiment, an effective amount of an agent that selectively inhibits the interaction between a degradation-prone CFTR and Dab2 is administered to a subject in need of treatment thereby preventing or treating the subject's cystic fibrosis. Subjects benefiting from treatment with an agent of the invention include subjects confirmed as having CF, subjects suspected of having CF, or subjects at risk of having CF (e.g., subjects with a family history).

Cystic Fibrosis is known to result from the dysfunction of CFTR due to mutations in the gene. While the most common mutations involve a deletion of phenylalanine in position 508, other mutations have been described (Grasemann & Ratjen (2010) *Expert Opin. Emerg. Drugs* 15:653-659; Pettit & Johnson (2011) *Ann. Pharmacother.* 45:49-59). These can be classified according to the effect they have on the CFTR (Table 3). In one aspect, the subject benefiting from treatment in accordance with the present invention expresses a degradation-prone CFTR (Class II mutation), such as ΔF508, ΔI507 or N1303K.

TABLE 3

| Class | Description |
|---|---|
| I | Defective or absence of CFTR protein synthesis with premature termination of CFTR production |
| II | Impaired processing: typically a defect in protein trafficking and degradation by the endoplasmic reticulum |
| III | Defective regulation: the CFTR reaches the apical cell surface but is not activated by ATP or cAMP |
| IV | Impaired function: transport of chloride ions is reduced at the apical membrane |
| V | Reduced synthesis of normal functioning CFTR |

Jones & Helm (2009) *Drugs* 69: 2003-2010; Grasemann & Ratjen (2010) *supra*; O'Sullivan & Freedman (2009) *Lancet* 373: 1991-2004.

Successful clinical use of a selective inhibitor of the invention can be determined by the skilled clinician based upon routine clinical practice, e.g., by monitoring frequency of respiratory infections and/or coughing; or changes in breathing, abdominal pain, appetite, and/or growth according to methods known in the art.

Agents disclosed herein can be employed as isolated and purified molecules (i.e., purified peptides, derivatives, peptidomimetics or small organic molecules), or in the case of peptides, be expressed from nucleic acids encoding said peptides. Such nucleic acids can, if desired, be naked or be in a carrier suitable for passing through a cell membrane (e.g., DNA-liposome complex), contained in a vector (e.g., plasmid, retroviral vector, lentiviral, adenoviral or adeno-associated viral vectors and the like), or linked to inert beads or other heterologous domains (e.g., antibodies, biotin, streptavidin, lectins, etc.), or other appropriate compositions. Thus, both viral and non-viral means of nucleic acid delivery can be achieved and are contemplated. Desirably, a vector used in accordance with the invention provides all the necessary control sequences to facilitate expression of the peptide. Such expression control sequences can include but are not limited to promoter sequences, enhancer sequences, etc. Such expression control sequences, vectors and the like are well-known and routinely employed by those skilled in the art.

For example, when using adenovirus expression vectors, the nucleic acid molecule encoding a peptide can be ligated to an adenovirus transcription/translation control complex, e.g., the late promoter and tripartite leader sequence. Alternatively, the vaccinia virus 7.5K promoter can be used. (see, e.g., Mackett, et al. (1982) *Proc. Natl. Acad. Sci. USA* 79:7415-7419; Mackett, et al. (1984) *J. Virol.* 49:857-864; Panicali, et al. (1982) *Proc. Natl. Acad. Sci. USA* 79:4927-4931). Mammalian expression systems further include vectors specifically designed for "gene therapy" methods including adenoviral vectors (U.S. Pat. Nos. 5,700,470 and 5,731,172), adeno-associated vectors (U.S. Pat. No. 5,604,090), herpes simplex virus vectors (U.S. Pat. No. 5,501,979) and retroviral vectors (U.S. Pat. Nos. 5,624,820, 5,693,508 and 5,674,703 and WIPO publications WO 92/05266 and WO 92/14829).

In particular embodiments, the CFTR-Dab2 inhibitors of the invention are used in a combination therapy with at least one other agent employed in the treatment of cystic fibrosis, including molecules that ameliorate the signs or symptoms of cystic fibrosis. Other agents of use in the combination therapy include, but are not limited to CFTR correctors, CFTR potentiators, CAL inhibitors, mucolytics and anti-inflammatory agents.

CFTR correctors are molecules that correct one or more defects found in Class II mutations by rescuing proteins from endoplasmic reticulum degradation, improving trafficking of CFTR to the cell surface, and/or inhibiting proteins that are involved in the recycling of CFTR in the cell membrane. Several correctors have been identified using high throughput assays (O'Sullivan & Freedman (2009) *Lancet* 373:1991-2004). For example, Ataluren (3-[5-(2-Fluorophenyl)-1,2,4-oxadiazol-3-yl]benzoic acid) can cause ribosomal read-through of premature stop mutations in patients with class I mutations, correct the processing of CFTR, and thereby increase the production of functional CFTR (Jones & Helm (2009) *Drugs* 69:2003-2010; Wilschanski, et al. (2011) *Eur. Respir. J.* 38:59-69). Lumacaftor (VX-809; 3-{6-{[1-(2,2-difluoro-1,3-benzodioxol-5-yl)cyclopropanecarbonyl]amino}-3-methylpyridin-2-yl}benzoic acid) is another corrector that acts as a "chaperone" to assist the movement of defective CFTR to the epithelial cell membrane (Jones & Helm (2009) *Drugs* 69:2003-2010; O'Sullivan & Freedman (2009) supra). Indeed, it has been shown that Lumacaftor can restore the Po of ΔF508-CFTR to near wild-type levels (Van Goor, et al. (2011) supra). Lumacaftor can be provided in any suitable form including, but not limited to tablet, capsule, injectable, or aerosol. Dosing of Lumacaftor can be in the range of 200 to 600 mg once daily. Another corrector is corr-4a (N-(2-(5-Chloro-2-methoxy-phenylamino)-4'-methyl-[4,5']bithiazolyl-2'-yl)-benzamide), which increases F508Δ-CFTR cell-surface expression and increases chloride conductance.

A CFTR potentiator enhances the activity of CFTR that is correctly located at the cell membrane. CFTR potentiators are particularly useful in the treatment of subjects with class III mutations. CFTR potentiators of use in this invention include certain flavones and isoflavones, such as genistein, which are capable of stimulating CFTR-mediated chloride transport in epithelial tissues in a cyclic-AMP independent manner (See U.S. Pat. No. 6,329,422, incorporated herein by reference in its entirety); phenylglycine-01 (2-[(2-1H-indol-3-yl-acetyl)-methylamino]-N-(4-isopropylphenyl)-2-phenylacetamide); felodipine (Ethyl methyl 4-(2,3-dichlorophenyl)-2,6-dimethyl-1,4-dihydro-3,5-pyridinedicarboxylate); sulfonamide SF-01 (6-(ethylphenylsulfamoyl)-4-oxo-1,4-dihydroquinoline-3-carboxylic acid cycloheptylamide); and UCCF-152 (3-[2-(benzyloxy)phenyl]-5-(chloromethyl) isoxazole). Ivacaftor (VX-770; N-(2,4-Di-tert-butyl-5-hydroxyphenyl)-4-oxo-1,4-dihydroquinoline-3-carboxamide) has also been shown to increase CFTR channel open probability (Po) in both the F508Δ processing mutation and the G551D gating mutation (Van Goor, et al. (2011) supra). Ivacaftor can be provided, e.g., in tablet form (KALYDECO; 150 mg Ivacaftor) or alternatively in any other suitable form, e.g., as an aerosol, capsule or injectable. Dosing of Ivacaftor can, e.g., include 250 mg Ivacaftor every 12 hours.

In some embodiments, the other agent is a single compound with dual corrector and potentiator activities. Such agents include VRT-532 (3-(2-hydroxy-5-methylphenyl)-5-phenylpyrazole) and cyanoquinolines such as N-(2-((3-Cyano-5,7-dimethylquinolin-2-yl)amino)ethyl)-3-methoxybenzamide (CoPo-2), as well as hybrid bithiazole-phenylglycine corrector-potentiators which, when cleaved by intestinal enzymes, yield an active bithiazole corrector and phenylglycine potentiator (Mills, et al. (2010) *Bioorg. Med. Chem. Lett.* 20:87-91).

In addition, this invention includes the use of Dab2 inhibitors in combination with CAL inhibitors such as those described in US 2014/0100155 and U.S. Pat. No. 8,415,292, which is incorporated herein by reference in its entirety. A CAL inhibitor prevents the interaction of CFTR with the CFTR Associated Ligand (CAL), a PDZ protein that binds to the C-terminus of CFTR (Cheng, et al. (2002) *J. Biol. Chem.* 277:3520-9; Wolde, et al. (2007) *J. Biol. Chem.* 282:8099-109; Cushing, et al. (2010) *Agnew Chem. Int. Ed. Engl.* 49:9907-22). CAL facilitates the post-endocytic lysosomal degradation of CFTR. CAL inhibitors include both peptides and small molecules. CAL inhibitors have been identified by peptide-array screening and by screening of small-molecule libraries for the disruption of the interaction between the CAL PDZ domain and a fluorescently labeled reporter peptide. See US 2014/0100155 and U.S. Pat. No. 8,415,292.

Mucolytics are agents that dissolve thick mucus by dissolving various chemical bonds within secretions, which in turn can lower the viscosity by altering the mucin-containing components. Mucolytics of use in this invention include, but are not limited to acetylcysteine ((2R)-2-acetamido-3-sulfanylpropanoic acid), ambroxol (trans-4-(2-Amino-3,5-dibrombenzylamino)-cyclohexanol), bromhexine (2,4-dibromo-6-{[cyclohexyl(methyl)amino]methyl}aniline), carbocisteine (R)-2-Amino-3-(carboxymethylsulfanyl)propanoic acid), domiodol ([2-(iodomethyl)-1,3-dioxolan-4-yl]methanol), dornase alfa (recombinant human deoxyribonuclease I), eprazinone (3-[4-(2-ethoxy-2-phenyl-ethyl) piperazin-1-yl]-2-methyl-1-phenyl-propan-1-one), erdosteine (2-[(2-oxothiolan-3-yl)carbamoylmethylsulfanyl]acetic acid), letosteine (2-{2-[(2-ethoxy-2-oxoethyl) thio]ethyl}-1,3-thiazolidine-4-carboxylic acid), mannitol, mesna (sodium 2-sulfanylethanesulfonate), neltenexine (N-(2,4-dibromo-6-{[(4-hydroxycyclohexyl)amino] methyl}phenyl)thiophene-2-carboxamide), and sobrerol ((1S)-5-(1-hydroxy-1-methylethyl)-2-methylcyclohex-2-en-1-ol), stepronin (N-{2-[(2-thienylcarbonyl)thio] propanoyl}glycine).

Inflammation is a major component of cystic fibrosis. If untreated, inflammation can irreversibly damage the airways, leading to bronchiectasis and ultimately respiratory failure. Anti-inflammatory drugs used in the treatment of cystic fibrosis include steroids such as corticosteroids and nonsteroidal anti-inflammatory drugs such as ibuprofen.

Other agents include pentoxifylline and azithromycin, which, in addition to its antimicrobial effects, also possesses anti-inflammatory properties.

Other therapeutics of use in combination with the agents of this invention include, but are not limited to, 2,2-dimethyl butyric acid (U.S. Pat. No. 7,265,153); glycerol, acetic acid, butyric acid, D- or L-amino-n-butyric acid, alpha- or beta-amino-n-butyric acid, arginine butyrate or isobutyramide, all disclosed in U.S. Pat. Nos. 4,822,821 and 5,025,029; and butyrin, 4-phenyl butyrate, phenylacetate, and phenoxy acetic acid, disclosed in U.S. Pat. No. 4,704,402.

The combination therapy of this invention preferably includes (a) at least one agent that selectively inhibits the interaction between a degradation-prone CFTR and Dab2 and (b) a CFTR corrector, CFTR potentiator, CAL inhibitor, mucolytic, anti-inflammatory agent, or combination thereof. In some embodiments, the combination therapy of this invention includes (a) at least one agent that selectively inhibits the interaction between a degradation-prone CFTR and Dab2 and (b) a CFTR corrector, CFTR potentiator, CAL inhibitor, or combination thereof. In accordance with this invention, the active agents of the combination therapy can be administered simultaneously of consecutively, within seconds, minutes, hours, days or weeks of each other. It is expected that the above-referenced combination therapy will have an additive or synergistic effect in the treatment of cystic fibrosis. In particular, it is expected that the combination of a selective inhibitor of the CFTR and Dab2 interaction, a CFTR corrector, and a CFTR potentiator will reverse all three defects (folding, gating, and stability) of $\Delta$F508-CFTR.

The present invention also provides a kit containing (a) an agent for inhibiting the interaction between a degradation-prone CFTR and Dab2 in combination with (b) a CFTR corrector, CFTR potentiator, CAL inhibitor, mucolytic, anti-inflammatory agent, or combination thereof, for use in the prevention or treatment of cystic fibrosis. In some embodiments, the kit includes a plurality of separate containers, each containing at least one active agent useful in a combination therapy for the prevention or treatment of cystic fibrosis. The kit contains a first container containing an agent for inhibiting the interaction between a degradation-prone CFTR and Dab2. The kit further includes a container for a CFTR corrector, a container for a CFTR potentiator, a container for a mucolytic, and or a container for an anti-inflammatory agent. The containers of the kit may be enclosed within a common outer packaging, such as, for example a cardboard or plastic box or a shrink wrap outer skin enclosing the various containers. In certain embodiments, the agent for inhibiting the interaction between a degradation-prone CFTR and Dab2; and CFTR corrector, CFTR potentiator, CAL inhibitor, mucolytic, and/or anti-inflammatory agent are each individually formulated in an acceptable carrier. The kit may be in the form of a consumer package or prescription package which provides the products described above. The package may provide instructions or directions on how to use and/or combine the products for one or more treatment regimens.

For therapeutic use, active agents of the invention can be formulated with a pharmaceutically acceptable carrier at an appropriate dose. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically acceptable carrier, composition or vehicle, such as a liquid or solid filler, diluent, excipient, or solvent encapsulating material, is involved in carrying or transporting the subject agent from one organ, or portion of the body, to another organ, or portion of the body. Each carrier must be acceptable in the sense of being compatible with the other ingredients of the formulation and not injurious to the patient.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Compositions of the present invention can be administered parenterally (for example, by intravenous, intraperitoneal, subcutaneous or intramuscular injection), topically including via inhalation, transdermally, orally, intranasally, intravaginally, or rectally according to standard medical practices. In particular embodiments, the compositions of the present invention are formulated for administration via inhalation, e.g., as aerosol preparations including solutions or solids in powder form, which may be in combination with an inert compressed gas such as nitrogen.

The selected dosage level of an agent will depend upon a variety of factors including the activity of the particular agent of the present invention employed, the route of administration, the time of administration, the rate of excretion or metabolism of the particular agent being employed, the duration of the treatment, other drugs, compounds and/or materials used in combination with the particular agent employed, the age, sex, weight, condition, general health and prior medical history of the patient being treated, and other factors well-known in the medical arts.

A physician having ordinary skill in the art can readily determine and prescribe the effective amount of the pharmaceutical composition required based upon the administration of similar compounds or experimental determination. For example, the physician could start doses of an agent at levels lower than that required in order to achieve the desired therapeutic effect and gradually increase the dosage until the desired effect is achieved. This is considered to be within the skill of the artisan and one can review the existing literature on a specific agent or similar agents to determine optimal dosing.

The fact that other proteins destined for the intracellular transport pathway frequently exhibit transport delays due to mutations, or other factors, indicates that the cell-surface expression of such degradation-prone proteins may also be mediated by Dab2. Thus, it is contemplated that the agents of this invention can also be used to induce or increase the cell surface expression of other degradation-prone proteins. Accordingly, physiological disorders associated with other degradation-prone proteins besides CFTR can similarly be treated using the methods disclosed herein. Physiological disorders associated with a degradation-prone protein that can be treated in a method of the invention include, for example, Stargardt's disease and particular types of macular dystrophy caused by mutations of the retinal rod transporter, ABC-R, resulting in deficiency of export.

The invention is described in greater detail by the following non-limiting examples.

Example 1: MATERIALS AND METHODS

Cell Culture. CFBE41o- cells stably expressing wild-type (WT) CFTR or ΔF508 mutant (ΔF508) CFTR under the control of a cytomegalovirus promoter are described in the art (Bebok, et al. (2005) *J. Physiol.* 569:601-615). Cells were maintained in MEM with 2 mM L-glutamine, 10% fetal bovine serum, 50 U/mL penicillin, 50 μg/mL streptomycin, 2 μg/mL puromycin, and 5 μg/mL plasmocin. Cells were grown at 37° C. in a 5% $CO_2$ incubator. All cells used in experiments were between passages 12 and 28.

Peptide Synthesis. All peptides were synthesized by Tufts' (Keck) peptide synthesis core facility. F*- and BT- prefixes indicate peptides with N-terminal fluorescein or biotin moiety, respectively.

Protein Expression and Purification. The DH domain of human Dab2 (UniProt Accession No. P98082-1, residues 33-191) was subcloned by PCR into the pET16b expression vector and expressed in *E. coli* BL21 (DE3) RIL cells grown overnight at 20° C. in LB medium following induction with 0.1 M IPTG. Cell pellets were ruptured in a Microfluidizer shear cell in lysis buffer (50 mM Tris pH 8.5, 150 mM NaCl, 1 mM DTT, 2 mM $MgCl_2$, 0.1 mM ATP, 25 U/ml Benzonase, EDTA-free Complete Protease Inhibitor tablet). Lysates were clarified by centrifugation at 40,000 rpm in a Ti45 rotor for 1 hour at 4° C. A final concentration of 40 mM imidazole was added to the supernatant before application to a 5 ml HISTRAP HP column (GE Healthcare), which had been pre-equilibrated with 10 column volumes (CV) of NINTA A buffer (40 mM imidazole pH 8.5, 25 mM Tris pH 8.5, 150 mM NaCl, 1 mM DTT, 0.1 mM ATP). After sample application, the column was washed with 50 CV of NINTA A buffer followed by 30 CV of 15% NINTA B buffer (400 mM imidazole pH 8.5, 25 mM Tris pH 8.5, 150 mM NaCl, 1 mM DTT, 0.1 mM ATP). The protein was then eluted along a gradient of 25-80% NINTA B over 35 CV. Eluates were collected in tubes containing 100 μL of 0.5 M EDTA, pH 8.0.

Metal-affinity eluates were applied to a HILOAD SUPERDEX 75 prep grade 26/60 size-exclusion chromatography (SEC) column (GE Healthcare) in 25 mM Tris pH 8.5, 150 mM NaCl, 1 mM DTT, 0.02% $NaN_3$. Following SEC purification, the N-terminal polyhistidine tag was cleaved by incubating the protein with rhinovirus 3C protease at a 1:50 mass ratio overnight at 4° C. A final concentration of 60 mM imidazole was added to the mixture, which was then applied to a 5 ml HISTRAP HP column pre-equilibrated with 10 CV of NINTA buffer to recover the tag-free protein in the flow through. Buffers used for the second HISTRAP purification are the same as the buffers described in the earlier purification step except for adding 60 mM imidazole to the sample before loading and to the NINTA buffer and using Tris pH 8.0 instead of pH 8.5. Protein was concentrated using AMICON Ultra-15 10000 MWCO (Millipore) and then dialyzed into 25 mM Tris pH 8.0, 150 mM NaCl, 1 mM DTT, 5% glycerol and 0.02% $NaN_3$. SDS-PAGE and analytical SEC were used to assess the purity and oligomeric-homogeneity of the purified protein, respectively. Protein stocks were flash-frozen in liquid nitrogen and stored at −80° C.

Circular Dichroism. CD spectra were determined using 10 μM protein concentrations in 150 mM NaCl and 25 mM $NaH_2PO_4/Na_2HPO_4$ pH 7.4. Thermal denaturation was monitored at temperature increment steps of 1° C. from 5 to 85° C. and wavelengths of 208, 215, and 22 nm. For the CD spectra of peptide-bound protein, 15 μM peptide was incubated with 10 μM protein for 30 minutes before the measurements. DMSO concentration did not exceed 0.0075%. Analysis of denaturation curve and calculation of melting temperature (Tm) was according to known methods (Mergny & Lacroix (2003) *Oligonucleotides* 13:515-37).

Fluorescence Polarization. Fluorescence polarization (FP) data were measured on a microplate reader (Tecan Infinite M1000, Mannedorf, Switzerland) at 27° C. For $K_d$ measurements, serially diluted protein in FP buffer (25 mM Tris pH 8.0, 150 mM NaCl, 1 mM DTT, and 0.02% (w/v) $NaN_3$) supplemented with 0.1 mg/mL bovine IgG (Sigma) and 0.5 mM THESIT (Fluka) is dispensed into HE low-volume, black 96-well plates (Molecular Devices) and mixed with 3 nM of fluorescently labeled peptide, F*-STA02, pre-equilibrated with FP buffer in the dark for 10-15 minutes. Plates were mixed by vibration, centrifuged for 2 minutes at 1200 g to remove air bubbles and allowed to equilibrate for 30 minutes at room temperature before measurement. For competition binding experiments, protein at a concentration of 1-3×$K_d$ was equilibrated with 3 nM fluorescently labeled reporter peptide for 30 minutes at room temperature. Unlabeled competitor peptides were serially diluted and mixed with the protein-reporter mix. Plates were mixed by vibration, centrifuged at 1200 g for 2 minutes and allowed to equilibrate at room temperature for 30 minutes before measurement. Fluorescence polarization was measured at an excitation wavelength of 470±5 nm and an emission wavelength of 525±20 nm as:

$$FP_{exp} = \frac{I_{vv} - gI_{vh}}{I_{vv} + gI_{vh}}$$

where $I_{vv}$ and $I_{vh}$ represent the vertically and horizontally polarized light emitted as a result of fluorophore excitation with vertically polarized light and g represents the assay- and machine-specific bias. The time of equilibration, salt, detergent, and carrier protein concentrations were all empirically optimized. Fluorescence intensities were monitored and percent change ranged from 5-15% excluding any significant reporter fluorescence quantum yield change or light-scattering artifacts. Other reading parameters include: gain of 60, number of flashes of 50, and settling time of 300 ms. For analysis purposes, data were converted to fluorescence anisotropy values.

Direct binding data were fit to a single-site equilibrium-binding model.

$$P + L \xrightleftharpoons{K_d} PL$$

A non-linear least-squares algorithm (Kaleidagraph) was used to fit the experimental anisotropy data ($r_{exp}$) to the anisotropy calculated using the following equation:

$$r_{calc} = r_L + (r_{PL} - r_L)[PL]/[L]_{tot}$$

where $[L]_{tot}$=total reporter peptide concentration, $r_L$ and $r_{PL}$=the fluorescence anisotropies of the free and bound ligands, respectively, and [PL]=concentration of protein: ligand complex. [PL] was determined as:

$$[PL] = \frac{[L]_{tot} + [P]_{tot} + K_d \sqrt{([L]_{tot} + [P]_{tot} + K_d)^2 - 4[L]_{tot} + [P]_{tot}}}{2}$$

where $[P]_{tot}$=total protein concentration and $K_d$=equilibrium dissociation constant of [PL]. Competition isotherms were fit using a non-linear least-squares algorithm implemented in EXCEL using the SOLVER function. $r_{exp}$ was fit to:

$$r_{calc} = \frac{r_L + r_{PL}[P]/K_d}{1 + [P]/K_d}$$

where the free protein concentration [P] in the presence of both the reporter and competitive inhibitor was calculated as a function of the total protein and ligand concentrations and the equilibrium dissociation constant $K_d$ (known) and $K_i$ (fit), respectively, by exact analytical solution of the resulting cubic equation (Wang, et al. (1995) *Biotechnol. Prog.* 11:558-64).

Isothermal Titration calorimetry. Dab2-DH protein was dialyzed versus 150 mM NaCl, 25 mM Tris pH 8.0, and 0.02% $NaN_3$ or 150 mM NaCl, 25 mM $NaH_2PO_4/Na_2HPO_4$ pH 7.4, and 0.02% $NaN_3$. Peptides were solubilized in recovered and degassed dialysis buffer. Peptide stocks were in 100% DMSO, which resulted in 1-2% DMSO in the isothermal titration calorimetry (ITC)-peptide solution. Thus, to maintain a constant DMSO concentration between the cell chamber (protein solution) and the syringe (peptide solution), 1-2% DMSO was added to the ITC-protein solution. Experiments were performed at 15, 25, or 35±0.2° C. on a MICROCAL VP-ITC calorimeter. A 2 µL peptide injection over 4.1 seconds preceded 30-10 µL injections over 300 seconds each. The system was allowed to equilibrate (reach baseline) between injections for 300 seconds while stirring at a speed of 300 rpm. ITC thermograms were fit to a single-site binding model using Origin software package v11. The ITC data were presented by showing the baseline-adjusted titration as heat flow versus time (top) and the peak-integrated concentration-normalized molar heat flow per injection versus the peptide: protein molar ratio (bottom). To account for the contribution of protein, peptide, and buffer protonation enthalpies to the binding enthalpies and consequently the binding constants, titrations in buffers with known and distinct heats of ionization (Tris and Phosphate buffers) were conducted.

Peptide Pull-down and Western Blotting. Streptavidin-paramagnetic particles (Promega) were washed twice with wash buffer (50 mM Tris pH 8.0, 150 mM NaCl, 2 mM EGTA, 2 mM EDTA, 5% glycerol, 1 mM DTT) and incubated with 20 µM BT-STA02 (N-terminally biotinylated STA02) for 1 hour on a rotator at 4° C. Beads were then washed twice with wash buffer and once with lysis buffer (50 mM Tris pH 8.0, 150 mM NaCl, 2 mM EGTA, 2 mM EDTA, 5% glycerol, 1 mM DTT, 1% IGEPAL, complete protease inhibitor tablet (Roche)) before incubation with cell lysate. CFBE cells were washed twice with cold PBS, incubated with lysis buffer for 20 minutes shaking at 4° C., scraped, passed through a 27G1/2 syringe, and spun at 13000 rpm for 15 minutes at 4° C. The supernatant was incubated with BT-STA02-coated beads for 2 hours on a rotator at 4° C. Beads were then washed twice with wash buffer and bound protein was eluted with Laemmli sample buffer (Bio-Rad) at 45° C. for 10 minutes. Samples were run on a 7.5% SDS-PAGE gel and probed with anti-Dab2 (BD Biosciences) or anti-p96 Dab2 (Epitomics).

Peptide SPOT Arrays. 15-mer SPOT peptide cellulose membrane arrays were synthesized according to the SPOT-synthesis method at the Koch Institute (MIT). Arrays were first hydrated with ethanol for 10 minutes and then washed 3 times with Tris-buffered saline (TBS), pH 7.0 (50 mM Tris-base, 138 mM NaCl, 2.7 mM KCl) for 10 minutes each. Membranes were then incubated overnight at 4° C. with membrane-blocking solution (MBS) (20% [v/v] of casein-based blocking buffer concentrate 10×(Sigma-Genosys) in TBST pH 8.0 (0.05% TWEEN-20 and 5% sucrose in TBS)). Membranes were then washed with TBS for 10 minutes and incubated with purified polyhistidine-tagged Dab2-DH protein at 200 µg/mL diluted in MBS, overnight at 4° C. Membranes were then washed 3 times with TEST for 10 minutes each and then incubated with anti-polyhistidine antibody (H1029, sigma) for 2 hours at room temperature followed by 3 washing steps with TEST for 10 minutes each. Membrane was then incubated with anti-mouse secondary-HRP for 1 hour at room temperature. Before incubation with the membrane, oligomeric homogeneity of the protein was tested with analytical SEC.

High-Throughput Small Molecule Screen. The library screen was performed at the Broad Institute. Compound transfers were done using a 384-well pin tool equipped with 100 nL hydrophobic surface-coated pins. DMSO (100 nL, negative control), STA02 (positive control), or library compounds were dispensed into 20 µL of protein (200 nM) and reporter (F*-STA02, 30 nM) mixture with 0.1 mg/ml mouse IgG and 0.5 mM THESIT. Final concentrations in the mixture were DMSO (1%), STA02 (20 µM), and compounds (18 µM). Plates were incubated for 35-45 minutes before reading on an LJL analyst HT plate reader. Detector settings were set to smart-read (PMT sensitivity=2), attenuator OUT and Z position=2.5 mm. Compounds were tested in duplicates on two separate plates. Positive and negative controls were included in each individual plate.

Fluorescence Polarization Competition Assay to Identify Small Molecule Inhibitors. For Competition binding experiments, 200 nM protein concentrations were equilibrated with fluorescently labeled peptide (F*-STA02, 30 nM) for 30 minutes at room temperature. Unlabeled competitor peptide (STA02) or compound hits were serially diluted and mixed with the protein-reporter mix. Percent DMSO in all samples was 1%. Plates were mixed by vibration, centrifuged at 1200 g for 2 minutes and allowed to equilibrate at room temperature for 30-45 minutes before measurement. Fluorescence polarization was measured at an excitation wavelength of 470±5 nm and an emission wavelength of 525±20 nm. Data analysis and calculation of binding affinities were as described above.

Toxicity and Cell Viability Assays. CFBE cells were seeded at $5 \times 10^3$ in 96-well plates. Cells were treated in fetal bovine serum (FBS)-free minimum essential medium (MEM, Gibco). Assays were performed and measured according to the CYTOTOX 96 Non-Radioactive cytotoxicity Assay (G1780) kit (Promega) and the CELLTITER 96 Aqueous One solution Cell proliferation Assay kit (Promega) instructions. Percent toxicity for the LDH assay was calculated as:

$$\% \text{ of Maximum Toxicity} = \frac{\text{Signal (Compound)} - \text{Signal (0.2\% } DMSO)}{\text{Signal (1\% TRITON)} - \text{Signal (0.2\% } DMSO)} \times 100$$

Cell survival was measured by the MTT assay and calculated as:

$$\% \text{ Survival of Control} = \frac{\text{Signal (Compound)}}{\text{Signal (0.2\% } DMSO)}$$

A background signal of 0.2% DMSO in media from a well without cells was subtracted from all readings before the above-referenced calculations.

Example 2: Peptide Arrays for Identifying a High Affinity Inhibitor of Dab2-DH

To design high affinity peptide binders of the Dab2-DH domain and to measure their binding constants, sufficient amounts of the Dab2-DH domain (residues 33-191) were purified. Since room temperature incubation was required at multiple steps of the biochemical analysis, the thermal stability of the Dab2-DH domain was tested using circular dichroism. Apo- and peptide-bound Dab2-DH exhibited melting temperatures ($T_m$) of 47.1 and 49.1° C., respectively, indicating that experimental room temperature incubations are below the melting temperature of the protein.

Using the wild-type amyloid precursor protein derived peptide (APP-10: Gln-Asn-Gly-Tyr-Glu-Asn-Pro-Thr-Tyr-Lys (SEQ ID NO:13) as a starting sequence, Dab2-DH amino-acid binding preferences were examined using peptide arrays with single and combinatorial amino-acid substitutions. Since extended peptides have been shown to contribute to binding affinity and specificity (Dvir, et al. (2012) *Proc. Natl. Acad. Sci. USA* 109:6916-21), the APP-10 peptide was extended to a 17-mer sequence spanning residue positions $P^{-6}$-$P^{+8}$. The tyrosine residue was denoted as $P^0$ while up- and down-stream residues were represented with negative and positive numbers, respectively.

To verify the validity of the arrays and to gauge the dynamic range of the assay, an alanine scan of the 17-mer sequence was performed. Alanine substitutions of the canonical Asn-Pro-Xaa-Tyr (SEQ ID NO:1) motif residues abolished binding; thus, verifying the critical role of these residues in binding. Therefore, these residues were left unchanged in subsequent arrays. More importantly, a range of binding signal intensities were detected; thus, assuring the ability to identify substitutions that contribute to various extents to the binding affinity.

Peptide arrays with single residue substitutions across the amino acid spectrum were probed for binding to purified Dab2-DH protein. Dab2-DH showed a strong preference for Phe at $P^{-5}$ instead of a Tyr. A major contribution to binding energy was detected with a Thr to Asn substitution at $P^{-1}$. Besides a minor increase in binding with a His residue at $P^{-1}$, all other amino acid changes either reduced binding or had no detectable effect. $P^{+1}$ on the contrary exhibited preferences for a broad spectrum of substitutions including small aliphatic (Val and Leu), aromatic (Phe), charged (Glu and Asp), and long polar residues (Gln, Asn, and His). However, Gln and Asn residues were the most favored resulting in an immensely stronger binding signal. By exploring preferences for further downstream residues, Phe at $P^{+2}$ conspicuously favored a Pro substitution. While no other downstream changes resulted in major increased binding, a select few were noticeable and merited consideration including $P^{+3}$, $P^{+5}$ and $P^{+8}$ substitutions to Gln, Asn, and Ala, respectively.

In addition to single substitutions, combinatorial changes at select positions were designed to survey potential pair-wise contributions to binding affinities. Further, beneficial multiple changes could be made to the wild-type peptide sequence toward achieving a high affinity peptide binder for Dab2-DH. Surveying DH domain preferences for amino-acid residues spanning $P^{-6}$-$P^{+8}$ suggested a strong preference for $P^{-5}$ aromatic, $P^{-4}$ negatively charged, $P^{-1}$ small aliphatic, and $P^{+1}$ positively charged residues (Howell, et al. (1999) *Mol. Cell. Biol.* 19:5179-88). Therefore, $Lys^{+1}$, $Gln^{+1}$, and $Arg^{+1}$ changes were explored along with a 20 amino acid scan of $P^{-1}$. Substituting $Lys^{+1}$ with Gln increased binding, but more importantly an Asn substitution at $P^{-1}$, preferred in the single substitution arrays, did not negatively affect the $Gln^{+1}$-induced change. An $Arg^{+1}$ substitution, on the other hand, dampened the positive effect of $Asn^{-1}$ on binding affinity. Although an additive effect of an $Asn^{-1}/Gln^{+1}$ versus a single $Gln^{+1}$ change was not detected, this double substitution did not have an adverse outcome on binding, as an $Arg^{+1}$ substitution did.

To evaluate upstream changes, $P^{-6}$, $P^{-5}$, and $P^{-4}$ combinatorial changes were selected. Increased binding was detected with a $Phe^{-5}$ substitution, which exhibited cooperatively enhanced binding with $Asp^{-4}$. A complete 20 amino acid scan of Gly at $P^{-6}$ failed to identify any more favorable residues either individually or in combination with a $Phe^{-5}$, $Asp^{-4}$, or $Phe^{-5}/Asp^{-4}$ substitution. Based on the peptide array findings, amino-acid changes favored by the Dab2-DH domain were incorporated into two novel peptides: STA01 and STA02 (Table 4). STA01 incorporated all selected substitutions upstream and including P+1. STA02 included the same substitutions as STA01 in addition to changes downstream of the P+1 residue.

TABLE 4

| Peptide | Sequence | SEQ ID NO: | $K_d \pm$ SD (nM) | $K_i \pm$ SD (nM) |
|---|---|---|---|---|
| WT APP | QNGYENPTYKFFEQMQN | 14 | | |
| STA01 | QNGFDNPNYKFFEQMQN | 3 | | 390 ± 87 |
| STA02 | QNGFDNPNYQPQENMQA | 4 | | 150 ± 36 |

TABLE 4-continued

| Peptide | Sequence | SEQ ID NO: | $K_d$ ± SD (nM) | $K_i$ ± SD (nM) |
|---|---|---|---|---|
| F*-STA02 | F*-AHAQNGFDNPNYQPQENMQA | 15 | 63 ± 10 | |
| BT-STA02 | BT-AHASGSGGFDNPNYQPQENMQA | 16 | | 155 |

$K_d$ and $K_i$ shown were measured at 27° C.
n > 3 for all titrations, except BT-STA02 n = 2.
BT denotes N-terminal biotin moiety.
F* denotes an FITC label.

Example 3: Biochemical Analysis of Peptide Binding Affinities

To verify and quantify the increase in binding affinity, fluorescence polarization (FP) assays were performed to measure the binding constants ($K_d$) of STA01 and STA02 to Dab2-DH. In the absence of protein, N-terminally fluorescein-labeled STA02 peptides (F*-STA02) exhibited low polarization values, which showed a dose-dependent shift upon incubation with increasing concentrations of Dab2-DH protein. This was indicative of protein:peptide complex formation with larger hydrodynamic radii compared to free F*-STA02. When converted to the related quantity of fluorescence anisotropy and fit to a single-site binding model, F*-STA02 yielded a binding affinity of 63±10 nM. To assess the influence of the fluorescein label on the binding affinity, a competitive displacement FP assay was performed using an unlabeled STA02 peptide. By fitting the data to the algorithm implemented on EXCEL using the SOLVER function, the $K_i$ value for STA02 was 150±36 nM. A similar experiment with an unlabeled STA01 peptide yielded a $K_i$ value of 390±87 nM. Thus, combining substitutions downstream of $P^{+1}$ in addition to the changes made to STA01, resulted in a 2-fold increase in binding affinity (STA02). F*-STA02 exhibited a 300-fold increase in binding affinity compared to the original APP 10-mer sequence. This implied that most of the gain in binding energy was contributed by substitutions made within and upstream of $P^{+1}$ and, relatively, only a minor increase in affinity was gained with the additional downstream changes. However, a peptide with changes only downstream of $P^{+1}$ would be a more direct approach to gauge the contribution of downstream residues to the peptide:Dab2-DH binding energy.

To quantify the thermodynamics of STA02 binding to the Dab2-DH domain and to confirm the binding constants using a non-fluorophore-dependent method, isothermal titration calorimetry (ITC) was performed. ITC experiments were carried out on the STA02 interaction with Dab2-DH in Tris and phosphate buffers at 25° C. The $K_d$ values in Tris and phosphate buffers were equal to 120.5±29.2 nM and 151 nM, respectively. The binding constants were comparable to the values obtained with the FP assay ($K_i$=150±36 nM). Because of distinct heats of ionization, performing the measurements in both Tris and phosphate buffers allowed for quantification of the net release of protons during binding ($N_{H+}$) as 0.04 per mole. Estimated ΔH and ΔS in Tris buffer were −20.7±1.45 Kcal/mol and −37.8 cal/mol/K, respectively. By measuring the ΔH of binding at 15, 25, and 35° C., a value of −320 cal/mol/K for the change of heat capacity, ΔCp was calculated. This implied a strong linear temperature dependence of the enthalpy. The $\Delta C_P$ measured for STA02:Dab2-DH complex formation was very comparable to that of other PTB domains (Farooq, et al. (1999) J. Biol. Chem. 274:6114-21; Mandiyan, et al. (1996) J. Biol. Chem. 271:4770-5). Extrapolation of $\Delta C_p$ to 37° C. (Fukada, et al. (1983) J. Biol. Chem. 258:13193-8) allowed for an estimation of a physiological $K_d$ value of 563 nM for unlabeled STA02, which was comparable to a $K_d$ of 220±52 nM measured by FP for F*-STA02. Interpreted in a Van't Hoff plot, the binding affinity was strongly temperature-dependent.

Therefore the binding interaction of STA02 to Dab2-DH was enthalpically driven with an estimated value of ΔG= −8.9 Kcal/mol, ΔH=−25.0 Kcal/mol, and TΔS=−16.1 Kcal/mol, at a physiological temperature of 37° C. Hence at a physiological temperature the binding was driven by a favorable enthalpy change.

Example 4: Dab2-DH Domain as a Biochemical Surrogate for Full-Length Dab2

Since Dab2 is a multi-modular adaptor protein, it was determined whether STA02 binding to the DH domain occurred with the full-length (FL) protein and in the context of other cellular interacting partners. To this end, the binding of STA02 to FL-Dab2 from bronchial epithelial (CFBE) cell lysates was tested in a pull-down assay. CFBE cell lysates were incubated with BT-STA02-coated streptavidin paramagnetic particles and bound protein were eluted and probed for Dab2 by western blot analysis. BT-STA02 binds to Dab2-DH with an affinity of 155±56 nM, while a scrambled version of the peptide (SCR02) did not bind and was thus used as a negative control. Only the p96-isoform of Dab2 bound to BT-STA02 while the shorter p67-isoform did not.

Example 5: High-Throughput Screen for Small Molecule Inhibitors of the Dab2-DH Domain One of the important implementations of the FP assay for screening is the competition assay. Protein was mixed with a reporter peptide and a library of compounds was screened for the ability to compete with the reporter, displacing it from the protein:reporter complex. For the optimization of the instant screen, Dab2-DH protein was incubated with a fluoresceinated peptide (F*-STA02, Table 4) at a concentration of ~3 $K_d$ (i.e., 200 nM). The binding of F*-STA02 peptide to the Dab2-DH domain was verified and the F*-STA02 peptide was used as a high-affinity reporter. DMSO and an unfluoresceinated version of the peptide STA02 were used as negative and positive controls, respectively.

The optimization of the signal-to-noise ratio in an assay minimizes the rate of false positives and negatives. An important statistical parameter used to evaluate the "suitability" of an assay for screening is the Z-factor. The Z-factor is a screening window parameter that reflects the dynamic range and the measurement variability of the assay (Zhang, et al. (1999) J. Biomol. Screen 4:67-73). Z'-factor is the statistical parameter calculated without the use of test compounds but rather with positive and negative controls (Zhang, et al. (1999) *J. Biomol. Screen* 4:67-73) as:

$$Z' = 1 - \frac{3\sigma_- + 3\sigma_+}{|\mu_+ - \mu_-|}$$

where $\sigma_+$, $\sigma_-$, $\mu_+$, and $\mu_-$ are the standard deviation and mean of positive (+) and negative (−) controls.

A 1>Z'≥0.5 range is reflective of an excellent assay (Zhang, et al. (1999) *J. Biomol. Screen* 4:67-73). This assay in 96-well plate format had a Z'=0.77 and its transfer to an automation-compatible format in 384-well plates maintained a Z'=0.76. Out of a 1600-compound library, six compounds (1-6) were active with five compounds exhibiting fluorescence intensities within the range of intensities observed for the positive and negative controls (Table 5).

TABLE 5

| Compound | Structure (IUPAC) | $K_i$ (µM) |
|---|---|---|
| 1 | (S(+)-10,11-Dihydroxyaporphine Hydrochloride) | 1.92 |
| 2 | (2-Hydroxyestradiol) | 1.26 |
| 3 | (5,5-dimethyl-5,6-dihydro [1,2,4]triazolo[3,4-a]isoquinoline-3(2H)-thione) | 0.779 |
| 4 | (4-(2,5-dimethoxyphenyl)-5-{[2-(2-pyridinyl)-1H-benzimidazol-1-yl]methyl}-4H-1,2,4-triazole-3-thiol) | n.a. |

TABLE 5-continued

| Compound | Structure (IUPAC) | $K_i$ (µM) |
|---|---|---|
| 5 | (Dipyridamole) | + |
| 6 | (5-benzyl-4-(3-methylphenyl)-4H-1,2,4-triazole-3-thiol) | n. a. | n.a., not active.
+, fluorescence change with FP.

To test the validity of these hits on a smaller scale and to quantify the binding potencies ($K_i$ values), an FP competition assay was carried out. Three compound hits, compounds 1, 2, and 3, had binding affinities ($K_i$) of 1.92 µM, 1.26 µM, and 779 nM, respectively. Compound 5 showed increased total fluorescence; however, the $K_i$ value was not obtained.

Example 6: Toxicity and Anti-Proliferative Profiles of Compound Hits

A toxicity assay (LDH) was used to test for the toxicity of the compounds on wild-type CF-derived bronchial epithelial (CFBE) cells. Cells treated with compounds 1 and 2 for 3 or 12 hours showed a similar dose-dependent toxicity profile at both time-points with toxicity reaching only 10% of maximum toxicity (1% TRITON) at a compound concentration of 40 µM. Compound 3 showed a similar toxicity profile only after 12 hours of treatment, but no toxicity after 3 hours. Toxicity of 100 µM compound concentrations at 3 hours did not exceed 10% of maximum toxicity. Longer treatment durations (24 hours) of compound 1 at 40 µM showed 20-40% toxicity. A cell viability assay (MTT) was used to measure the effect of the compounds on cell survival. Drug treatments for 3 or 12 hours at 100-5 µM did not cause significant reduction in cell survival.

Example 8: Physico-chemical Properties of Compound Hits

Potency, solubility and permeability are some of the critical attributes that determine the bioavailabilty and efficacy of small-molecule drugs. Lower drug solubility and permeability profiles are observed for molecules with molecular weights (MW)>500 Da, lipophilicity parameter (calculated Log P (C Log P))>5, number of H-bond donors >5, and number of H-bond acceptors >10 (100). None of the compounds deviated significantly from the favorable ranges for the Lipinski parameters (Table 6).

TABLE 6

| Compound | MW | CLogP[a] | Acceptor Count[b] | Donor Count[c] | #Lipinski Violations |
|---|---|---|---|---|---|
| 1 | 303.78 | 3.09 | 3 | 2 | 0 |
| 2 | 288.38 | 3.44 | 3 | 3 | 0 |
| 3 | 231.00 | 3.14 | 1 | 1 | 0 |
| 4 | 445.00 | 5.73 | 8 | 2 | 1 |
| 5 | 504.63 | 1.81 | 12 | 4 | 1 |
| 6 | 281.00 | 5.46 | 1 | 1 | 1 |

[a]CLogP < 5
[b]H-bond acceptor count < 10
[c]H-bond donor count < 5
MW < 500 Da

Example 7: Combination Therapies

Dab2 inhibitors, compounds 1, 2, 3 and 5 (20 µM) were evaluated in combination with Lumacaftor (VX809; 0.1 µM), a CFTR corrector, and Kalydeco, a CFTR potentiator. The results of this analysis indicated that 1 and 3 showed enhanced chloride currents in CFBE airway epithelial cells expressing the disease-associated ΔF508-CFTR mutant when used in parallel with VX809 (48 hours; FIG. 1) and Kalydeco (acutely). By ANOVA, the combination of compound 3 and VX809 produced a statistically significant benefit compared to VX809 (P<0.05). Given that these small-molecule inhibitors increase CFTR-mediated Cl⁻ currents across polarized human airway epithelial monolayers in combination with the corrector VX809, this combination is of use in the treatment of CF.

What is claimed is:

1. A peptide for inhibiting the interaction between a degradation-prone Cystic Fibrosis Transmembrane Conductance Regulator and Disabled-2 comprising the amino acid sequence of SEQ ID NO:2.

2. The peptide of claim 1, wherein the peptide has the amino acid sequence QNGFDNPNYQFFEQMQN (SEQ ID NO:3) or QNGFDNPNPYQPQENMQA (SEQ ID NO:4).

3. The peptide of claim 1, wherein the peptide is derivatized with a label, one or more post-translational modifications, a cell-penetrating sequence, or a combination thereof.

4. A pharmaceutical composition comprising the peptide of claim 1 in admixture with a pharmaceutically acceptable carrier.

5. The pharmaceutical composition of claim 4, wherein the composition is formulated for administration via inhalation.

6. A pharmaceutical composition comprising
   (i) a pharmaceutically acceptable carrier in admixture with a compound of Formula II, or hydrate, prodrug or pharmaceutically acceptable salt thereof:

Formula II

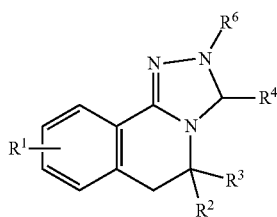

wherein
R¹ is present or absent, and when present is a substituent on one or more ring atoms and is for each ring atom independently a hydroxyl group, a halo group, or a substituted or unsubstituted lower alkyl or alkoxy group;
R², R³ and R⁶ are independently present or absent and when present independently represent hydrogen or a substituted or unsubstituted lower alkyl; and
R⁴ is =O or =S; and
(ii) a CFTR corrector, CFTR potentiator, CAL inhibitor, mucolytic, anti-inflammatory agent or a combination thereof.

7. A pharmaceutical composition comprising
(i) a pharmaceutically acceptable carrier in admixture with a compound of Formula III, or hydrate, prodrug or pharmaceutically acceptable salt thereof:

Formula III

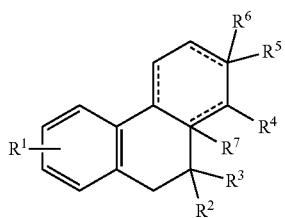

wherein
R¹ is present or absent, and when present is a substituent on one or more ring atoms and is for each ring atom independently a hydroxyl group, a halo group, or a substituted or unsubstituted lower alkyl or alkoxy group;
R², R³, R⁴, R⁵ and R⁶ are independently present or absent and when present independently represent hydrogen or a substituted or unsubstituted lower alkyl; or
R⁴ together with R³ or R⁵ form a substituted or unsubstituted cycloalkyl or heterocycloalkyl group;
R⁷ is a substituted or unsubstituted lower alkyl; and
dashed bonds are independently present or absent; and
(ii) a CFTR corrector, CFTR potentiator, CAL inhibitor, mucolytic, anti-inflammatory agent or a combination thereof.

8. The pharmaceutical composition of claim 6 or 7, wherein the composition is formulated for administration via inhalation.

9. The pharmaceutical composition of claim 4, further comprising a CFTR corrector, CFTR potentiator, CAL inhibitor, mucolytic, anti-inflammatory agent or a combination thereof.

10. A kit comprising
(a) an agent that inhibits the interaction between a degradation-prone Cystic Fibrosis Transmembrane Conductance Regulator (CFTR) and Disabled-2, wherein said agent comprises:
(i) a peptide having the amino acid sequence of SEQ ID NO:2,
(ii) a compound has the structure of Formula II:

Formula II

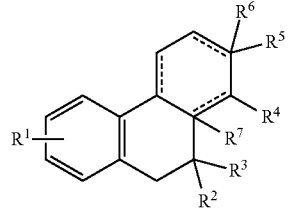

wherein
R¹ is present or absent, and when present is a substituent on one or more ring atoms and is for each ring atom independently a hydroxyl group, a halo group, or a substituted or unsubstituted lower alkyl or alkoxy group;
R², R³ and R⁶ are independently present or absent and when present independently represent hydrogen or a substituted or unsubstituted lower alkyl; and
R⁴ is =O or =S, or
(iii) a compound has the structure of Formula III:

Formula III

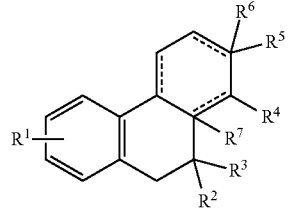

wherein
R¹ is present or absent, and when present is a substituent on one or more ring atoms and is for each ring atom independently a hydroxyl group, a halo group, or a substituted or unsubstituted lower alkyl or alkoxy group;
R², R³, R⁴, R⁵ and R⁶ are independently present or absent and when present independently represent hydrogen or a substituted or unsubstituted lower alkyl; or
R⁴ together with R³ or R⁵ form a substituted or unsubstituted cycloalkyl or heterocycloalkyl group;
R⁷ is a substituted or unsubstituted lower alkyl; and
dashed bonds are independently present or absent; and
(b) a CFTR corrector, CFTR potentiator, CAL inhibitor, mucolytic, anti-inflammatory agent or a combination thereof.

11. The kit of claim 10, wherein the peptide has the amino acid sequence QNGFDNPNYQFFEQMQN (SEQ ID NO:3) or QNGFDNPNPYQPQENMQA (SEQ ID NO:4).

12. The kit of claim 11, wherein the peptide is derivatized with a label, one or more post-translational modifications, a cell-penetrating sequence, or a combination thereof.

13. A method for treating cystic fibrosis comprising administering to a subject in need thereof a pharmaceutical composition comprising:
   (i) a peptide having the amino acid sequence of SEQ ID NO:2,
   (ii) a compound has the structure of Formula II:

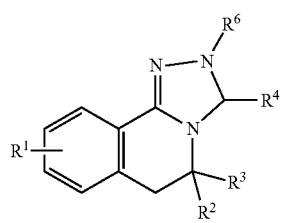

Formula II wherein
   $R^1$ is present or absent, and when present is a substituent on one or more ring atoms and is for each ring atom independently a hydroxyl group, a halo group, or a substituted or unsubstituted lower alkyl or alkoxy group;
   $R^2$, $R^3$ and $R^6$ are independently present or absent and when present independently represent hydrogen or a substituted or unsubstituted lower alkyl; and
   $R^4$ is =O or =S, or (iii) a compound has the structure of Formula III:

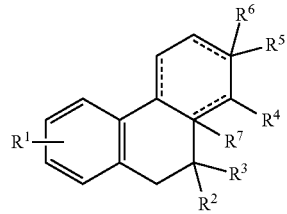

Formula III wherein
   $R^1$ is present or absent, and when present is a substituent on one or more ring atoms and is for each ring atom independently a hydroxyl group, a halo group, or a substituted or unsubstituted lower alkyl or alkoxy group;
   $R^2$, $R^3$, $R^4$, $R^5$ and $R^6$ are independently present or absent and when present independently represent hydrogen or a substituted or unsubstituted lower alkyl; or
   $R^4$ together with $R^3$ or $R^5$ form a substituted or unsubstituted cycloalkyl or heterocycloalkyl group;
   $R^7$ is a substituted or unsubstituted lower alkyl; and
   dashed bonds are independently present or absent, thereby treating the subject's cystic fibrosis.

14. The method of claim 13, further comprising administering to the subject a CFTR corrector, CFTR potentiator, CAL inhibitor, mucolytic, anti-inflammatory agent or a combination thereof.

* * * * *

SEQUENCE LISTING

```
<160> NUMBER OF SEQ ID NOS: 16

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 1

Asn Pro Xaa Tyr
1

<210> SEQ ID NO 2
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Xaa denotes Asn or His.
<220> FEATURE:
<221> NAME/KEY: MISC_FEATURE
<222> LOCATION: (9)..(9)
<223> OTHER INFORMATION: Xaa is Pro or absent.
<220> FEATURE:
<221> NAME/KEY: MISC_FEATURE
<222> LOCATION: (11)..(11)
<223> OTHER INFORMATION: Xaa denotes Val, Leu, Phe, Glu, Asp, Gln, Asn,
      or His.
<220> FEATURE:
<221> NAME/KEY: MISC_FEATURE
<222> LOCATION: (12)..(12)
<223> OTHER INFORMATION: Xaa denotes Pro or Phe.
<220> FEATURE:
<221> NAME/KEY: MISC_FEATURE
<222> LOCATION: (13)..(13)
<223> OTHER INFORMATION: Xaa denotes Phe or Gln.
<220> FEATURE:
<221> NAME/KEY: MISC_FEATURE
<222> LOCATION: (15)..(15)
<223> OTHER INFORMATION: Xaa denotes Ser, Thr, Asn or Gln.
<220> FEATURE:
<221> NAME/KEY: MISC_FEATURE
<222> LOCATION: (18)..(18)
<223> OTHER INFORMATION: Xaa denotes Asn or Ala.
```

```
<400> SEQUENCE: 2

Gln Asn Gly Phe Asp Asn Pro Xaa Xaa Tyr Xaa Xaa Xaa Glu Xaa Met
1               5                   10                  15

Gln Xaa

<210> SEQ ID NO 3
<211> LENGTH: 17
<212> TYPE: PRT
<213> ORGANISM: Artificial Sequence
<220> FEATURE:
<223> OTHER INFORMATION: Synthetic peptide

<400> SEQUENCE: 3

Gln Asn Gly Phe Asp Asn Pro Asn Tyr Gln Phe Phe Glu Gln Met Gln
1               5                   10                  15

Asn

<210> SEQ ID NO 4
<211> LENGTH: 18
<212> TYPE: PRT
<213> ORGANISM: Artificial Sequence
<220> FEATURE:
<223> OTHER INFORMATION: Synthetic peptide

<400> SEQUENCE: 4

Gln Asn Gly Phe Asp Asn Pro Asn Pro Tyr Gln Pro Gln Glu Asn Met
1               5                   10                  15

Gln Ala

<210> SEQ ID NO 5
<211> LENGTH: 27
<212> TYPE: PRT
<213> ORGANISM: Artificial Sequence
<220> FEATURE:
<223> OTHER INFORMATION: Synthetic peptide

<400> SEQUENCE: 5

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 6
<211> LENGTH: 8
<212> TYPE: PRT
<213> ORGANISM: Artificial Sequence
<220> FEATURE:
<223> OTHER INFORMATION: Synthetic peptide

<400> SEQUENCE: 6

Arg Arg Arg Arg Arg Arg Arg Arg
1               5

<210> SEQ ID NO 7
<211> LENGTH: 14
<212> TYPE: PRT
<213> ORGANISM: Artificial Sequence
<220> FEATURE:
<223> OTHER INFORMATION: Synthetic peptide

<400> SEQUENCE: 7

Gly Arg Lys Lys Arg Arg Gln Arg Arg Arg Pro Pro Gln Gln
1               5                   10
```

```
<210> SEQ ID NO 8
<211> LENGTH: 27
<212> TYPE: PRT
<213> ORGANISM: Artificial Sequence
<220> FEATURE:
<223> OTHER INFORMATION: Synthetic peptide

<400> SEQUENCE: 8

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 9
<211> LENGTH: 21
<212> TYPE: PRT
<213> ORGANISM: Artificial Sequence
<220> FEATURE:
<223> OTHER INFORMATION: Synthetic peptide

<400> SEQUENCE: 9

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 10
<211> LENGTH: 18
<212> TYPE: PRT
<213> ORGANISM: Artificial Sequence
<220> FEATURE:
<223> OTHER INFORMATION: Synthetic peptide

<400> SEQUENCE: 10

Lys Leu Ala Leu Lys Leu Ala Leu Lys Ala Leu Lys Ala Ala Leu Lys
1               5                   10                  15

Leu Ala

<210> SEQ ID NO 11
<211> LENGTH: 27
<212> TYPE: PRT
<213> ORGANISM: Artificial Sequence
<220> FEATURE:
<223> OTHER INFORMATION: Synthetic peptide

<400> SEQUENCE: 11

Gly Ala Leu Phe Leu Ala Phe Leu Ala Ala Ala Leu Ser Leu Met Gly
1               5                   10                  15

Leu Trp Ser Gln Pro Lys Lys Lys Arg Lys Val
            20                  25

<210> SEQ ID NO 12
<211> LENGTH: 16
<212> TYPE: PRT
<213> ORGANISM: Artificial Sequence
<220> FEATURE:
<223> OTHER INFORMATION: Synthetic peptide

<400> SEQUENCE: 12

Arg Gln Ile Lys Ile Trp Phe Gln Asn Arg Arg Met Lys Trp Lys Lys
1               5                   10                  15

<210> SEQ ID NO 13
<211> LENGTH: 10
```

```
<212> TYPE: PRT
<213> ORGANISM: Artificial Sequence
<220> FEATURE:
<223> OTHER INFORMATION: Synthetic peptide

<400> SEQUENCE: 13

Gln Asn Gly Tyr Glu Asn Pro Thr Tyr Lys
1               5                   10

<210> SEQ ID NO 14
<211> LENGTH: 17
<212> TYPE: PRT
<213> ORGANISM: Artificial Sequence
<220> FEATURE:
<223> OTHER INFORMATION: Synthetic peptide

<400> SEQUENCE: 14

Gln Asn Gly Tyr Glu Asn Pro Thr Tyr Lys Phe Phe Glu Gln Met Gln
1               5                   10                  15

Asn

<210> SEQ ID NO 15
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Conjugated to FITC

<400> SEQUENCE: 15

Ala His Ala Gln Asn Gly Phe Asp Asn Pro Asn Tyr Gln Pro Gln Glu
1               5                   10                  15

Asn Met Gln Ala
            20

<210> SEQ ID NO 16
<211> LENGTH: 22
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Conjugated to biotin.

<400> SEQUENCE: 16

Ala His Ala Ser Gly Ser Gly Gly Phe Asp Asn Pro Asn Tyr Gln Pro
1               5                   10                  15

Gln Glu Asn Met Gln Ala
            20
```